United States Patent
Koyama et al.

(10) Patent No.: US 9,808,205 B2
(45) Date of Patent: Nov. 7, 2017

(54) ABNORMALITY PREDICTION DEVICE, ABNORMALITY PREDICTION SYSTEM, ABNORMALITY PREDICTION METHOD, BIOLOGICAL INFORMATION MEASURING DEVICE, BIOLOGICAL INFORMATION MEASURING SYSTEM, AND WARNING NOTIFICATION METHOD

(71) Applicant: SEIKO EPSON CORPORATION, Tokyo (JP)

(72) Inventors: Fumio Koyama, Hara-mura (JP); Shinichiro Watanabe, Koto-ku (JP)

(73) Assignee: SEIKO EPSON CORPORATION, Tokyo (JP)

( * ) Notice: Subject to any disclaimer, the term of this patent is extended or adjusted under 35 U.S.C. 154(b) by 0 days.

(21) Appl. No.: 14/836,919

(22) Filed: Aug. 26, 2015

(65) Prior Publication Data

US 2016/0058394 A1    Mar. 3, 2016

(30) Foreign Application Priority Data

Aug. 27, 2014  (JP) .................................. 2014-172840
Nov. 13, 2014  (JP) .................................. 2014-231007

(51) Int. Cl.
*G08B 23/00* (2006.01)
*A61B 5/00* (2006.01)
(Continued)

(52) U.S. Cl.
CPC .......... *A61B 5/7275* (2013.01); *A61B 5/0002* (2013.01); *A61B 5/002* (2013.01);
(Continued)

(58) Field of Classification Search
CPC ... G06F 19/3418; A61B 5/002; A61B 5/0002; A61B 5/746
(Continued)

(56) References Cited

U.S. PATENT DOCUMENTS 5,544,649 A * 8/1996 David .................. A61B 5/6887
                                                     600/301
6,370,423 B1 * 4/2002 Guerrero ................ A61B 5/044
                                                     600/516
(Continued)

FOREIGN PATENT DOCUMENTS

JP   11-206721 A    8/1999
JP   2006-031433 A  2/2006
(Continued)

*Primary Examiner* — John A Tweel, Jr.
(74) *Attorney, Agent, or Firm* — Maschoff Brennan

(57) ABSTRACT

An abnormality prediction device includes a detection unit that detects detection information including at least one of biological information of a user and body motion information regarding a body motion of the user, a premonitory symptom determination unit (control unit) that determines whether a premonitory symptom has occurred in the user on the basis of the detection information detected by the detection unit and a premonitory pattern which is a pattern of the detection information according to the premonitory symptom of abnormality occurring in the user, and an information output unit (control unit) that, when the premonitory symptom determination unit determines that the premonitory symptom has occurred, outputs notification information indicating that occurrence of abnormality in the user is predicted.

20 Claims, 19 Drawing Sheets

(51) Int. Cl.
  *G06F 19/00* (2011.01)
  *A61B 5/044* (2006.01)
  *A61B 5/0402* (2006.01)
  *A61B 5/0456* (2006.01)
  *A61B 5/0476* (2006.01)
  *A61B 5/0488* (2006.01)

(52) U.S. Cl.
  CPC ............ *A61B 5/044* (2013.01); *A61B 5/7282* (2013.01); *A61B 5/742* (2013.01); *G06F 19/3418* (2013.01); *A61B 5/0402* (2013.01); *A61B 5/0456* (2013.01); *A61B 5/0476* (2013.01); *A61B 5/0488* (2013.01); *A61B 5/7246* (2013.01)

(58) Field of Classification Search
  USPC ............... 340/573.1; 600/300, 516; 702/187; 455/404.1
  See application file for complete search history.

(56) References Cited

U.S. PATENT DOCUMENTS

| | | | | |
|---|---|---|---|---|
| 8,007,436 | B2 * | 8/2011 | Katayama | A61B 5/411 600/300 |
| 8,254,853 | B2 * | 8/2012 | Rofougaran | A61B 5/055 455/404.1 |
| 8,868,616 | B1 * | 10/2014 | Otto | G06F 19/3418 455/404.1 |
| 9,055,925 | B2 * | 6/2015 | Paquet | A61B 5/6833 |
| 2008/0228088 | A1 | 9/2008 | Aubert et al. | |
| 2015/0305675 | A1 * | 10/2015 | Miller | A61B 5/0205 600/301 |

FOREIGN PATENT DOCUMENTS

| | | |
|---|---|---|
| JP | 2008-102884 A | 5/2008 |
| JP | 2009-505766 A | 2/2009 |

\* cited by examiner

ABNORMALITY PREDICTION DEVICE, ABNORMALITY PREDICTION SYSTEM, ABNORMALITY PREDICTION METHOD, BIOLOGICAL INFORMATION MEASURING DEVICE, BIOLOGICAL INFORMATION MEASURING SYSTEM, AND WARNING NOTIFICATION METHOD

This application claims priority to Japanese Patent Applications No. 2014-172840, filed Aug. 27, 2014, and No. 2014-231007, filed Nov. 13, 2014, the entireties of which are hereby incorporated by reference.

BACKGROUND

1. Technical Field

The present invention relates to an abnormality prediction device, an abnormality prediction system, an abnormality prediction method, a biological information measuring device, a biological information measuring system, and a warning notification method.

2. Related Art

Hitherto, there have been known portable body abnormality notification devices that detect biological information and positional information of a user and notifies, when the user's body is set to be in an abnormal state, the user and the like of the fact (for example, see JP-A-11-206721).

The portable body abnormality notification device disclosed in JP-A-11-206721 includes various types of biological information measuring sensors that detect and measure the blood pressure, pulse, and body temperature of a user, and a global positioning system (GPS) receiver that detects positional information of the user. The body abnormality notification device measures positional information and pieces of biological information when a measurement timing for each fixed cycle is set, and compares each of the pieces of biological information measured with a reference value (normal state value), an attentional state value, and an emergency state value. When it is determined that a user is set to be in an abnormal state on the basis of results of the comparison, an alarm is issued not only by displaying a caution message or the like on a display surface by flashing but also by ringing a buzzer.

When a response to the alarm is made by the operation of a button or the like, the body abnormality notification device displays a message asking whether to make contact on the display surface. When an instruction for making contact is given, personal identification information of a user and the measured biological information and positional information are automatically reported to the user's home by a phone function unit.

On the other hand, when there is no response to the alarm, information indicating emergency, personal identification information, positional information, measured biological information, and the pieces of past information thereof are automatically reported to a fire station for an ambulance.

It is possible to immediately cope with the abnormality of a user by such a portable body abnormality notification device.

In addition, there have been known daily life degree analysis systems that analyze living conditions of a person being monitored and detect and report abnormal changes in the living conditions (for example, see Japanese Patent No. 5070638).

The daily life degree analysis system disclosed in Japanese Patent No. 5070638 includes a living condition detection device, a going-out condition detection device, and a daily life degree analysis device. Among these devices, the living condition detection device indirectly detects living conditions of a person being monitored using a power sensor that measures the power consumption of an electrical product, a temperature sensor that measures the temperature of a heat source such as cooking equipment or a heating appliance, and a luminance sensor that measures the brightness of the surroundings. In addition, the going-out condition detection device detects going-out conditions of a person being monitored to thereby generate going-out information.

The daily life degree analysis device includes a feature amount extraction unit, a cycle flag conversion unit, a daily life degree analysis unit, a daily life degree evaluation unit, and an evaluation result output unit.

The feature amount extraction unit extracts a feature amount from detection information detected by the living condition detection device, and the cycle flag conversion unit converts date and time information into a cycle flag as category data. The daily life degree analysis unit performs multivariate analysis of a daily life degree using the feature amount, the cycle flag, and the above-mentioned going-out information. In the daily life degree evaluation unit, abnormal changes in the living conditions of a person being monitored are detected on the basis of the daily life degree analyzed by the daily life degree analysis unit. When the abnormal changes in the living conditions of the person being monitored are detected, the evaluation result output unit reports the fact to a monitoring person.

When abnormality occurs in daily life of a person being monitored, the occurrence of abnormality is reported to a monitoring person by such a daily life degree analysis system.

However, in the portable body abnormality notification device disclosed in JP-A-11-206721 mentioned above, an alarm is given notice of when a user is set to be in an abnormal state, and thus it is not possible to notify the user of a state in which the occurrence of abnormality is predicted. For this reason, if the user is notified of the occurrence of abnormality before the abnormality occurs, it is possible to take preliminary countermeasures such as the avoidance of danger with respect to the abnormality. However, since the user is notified of the occurrence of abnormality after the abnormality occurs, there is a problem in that it is difficult to take such countermeasures.

Incidentally, in a step in which there is a possibility of an abnormal change occurring in a person being monitored, when the person being monitored is notified of the purport, the person being monitored may take a preliminary action for responding to (coping with) the abnormal change.

However, the daily life degree analysis system disclosed in Japanese Patent No. 5070638 mentioned above reports, when the occurrence of an abnormal change in a living condition of a person being monitored is detected, reports the occurrence of the abnormal change to a monitoring person. For this reason, in a step in which there is a possibility of an abnormal change occurring in a person being monitored, it is not possible to notify the person being monitored and the monitoring person of the purport, and thus there is a problem in that it is difficult for the person being monitored to take action for coping with the abnormal change.

For this reason, there has been a demand for a configuration capable of allowing a person being monitored to easily take action for coping with an abnormal change.

SUMMARY

An advantage of some aspects of the invention is to provide an abnormality prediction device capable of outputting the fact that there is a possibility of abnormality occurring in a user, an abnormality prediction system, an abnormality prediction method, a biological information measuring device capable of notifying that there is a high possibility of abnormality occurring in a user, a biological information measuring system, and a warning notification method.

An abnormality prediction device according to a first aspect of the invention includes: a detection unit that detects detection information including at least one of biological information of a user and body motion information regarding a body motion of the user; a premonitory symptom determination unit that determines whether a premonitory symptom has occurred in the user on the basis of the detection information detected by the detection unit and a premonitory pattern which is a pattern of the detection information according to the premonitory symptom of abnormality occurring in the user; and an information output unit that, when the premonitory symptom determination unit determines that the premonitory symptom has occurred, outputs notification information indicating that occurrence of abnormality in the user is predicted.

Meanwhile, abnormality occurring in a user can include abnormality accompanied by fainting, epilepsy, and convulsions or at least one of impaired consciousness and a movement disorder due to a sudden onset caused by another disease.

According to the first aspect, it is determined whether a premonitory symptom has occurred on the basis of the detection information detected by the detection unit and the premonitory pattern which is a pattern (specific pattern of detection information) according to the premonitory symptom of the abnormality. When it is determined that the premonitory symptom has occurred, the notification information is output. Thereby, it is possible to output notification information indicating the occurrence of the abnormality is predicted, in a step before the abnormality occurs in the user. Therefore, it is possible to inform the user, the family of the user, or a medical worker that the occurrence of abnormality is predicted by notification of the notification information by the abnormality prediction device or an external device that receives the notification information. The notification information is notified to the user, and thus the user can take preliminary countermeasures such as an action of avoiding danger accompanied by the abnormality.

In the first aspect, it is preferable that the abnormality prediction device further includes a notification unit that notifies the user of the notification information which is input from the information output unit.

According to the first aspect with this configuration, the abnormality prediction device includes the notification unit that notifies the user of the notification information. Thus, when the occurrence of abnormality is predicted, it is possible to reliably notify the user of the purport. Therefore, the user can reliably take preliminary countermeasures.

In the first aspect, it is preferable that the abnormality prediction device includes a premonitory pattern storage unit that stores the premonitory pattern and a premonitory pattern updating unit that, when the abnormality occurs in the user, updates the premonitory pattern stored in the premonitory pattern storage unit on the basis of the detection information detected before an occurrence timing of the abnormality.

According to the first aspect with this configuration, a premonitory pattern serving as an index indicating whether a premonitory symptom of abnormality has occurred in a user is updated by the premonitory pattern updating unit on the basis of the detection information detected before the occurrence timing of the abnormality has occurred in the user. Thereby, it is possible to update the premonitory pattern on the basis of the detection information which is actually detected by the user. Therefore, it is possible to more accurately determine whether or not the premonitory symptom of the abnormality has occurred in the user.

In the first aspect, it is preferable that the abnormality prediction device further includes an abnormality determination unit that determines whether or not abnormality has occurred in the user, and when the abnormality determination unit determines that an abnormality has occurred, the premonitory pattern updating unit updates the premonitory pattern.

Here, when the abnormality determination unit determines that an abnormality has occurred, there is a high possibility that the premonitory symptom of the abnormality has occurred. For this reason, when the abnormality determination unit determines that the abnormality has occurred, the premonitory pattern updating unit updates the premonitory pattern, and thus it is possible to make it easier to extract the premonitory pattern according to the premonitory symptom from the detection information. Therefore, it is possible to automatically store an appropriate pattern according to the premonitory symptom as a premonitory pattern.

In the first aspect, it is preferable that the abnormality prediction device further includes an operation unit that receives an input operation from the user, and when an operation signal indicating the occurrence of the abnormality is input from the operation unit, the premonitory pattern updating unit updates the premonitory pattern.

According to the first aspect with this configuration, when an operation signal according to a user's input operation which indicates that abnormality has occurred is input, the premonitory pattern updating unit updates the premonitory pattern. Thereby, even when there is no abnormality determination unit, the abnormality prediction device can reliably ascertain that the abnormality has occurred in the user. Therefore, the premonitory pattern can be updated on the basis of the detection information which is actually detected before the operation signal is input, and thus it is possible to store a more appropriate premonitory pattern.

In the first aspect, it is preferable that the operation unit is configured to be able to input any one of an elapsed time since the abnormality has occurred in the user and an occurrence time of the abnormality, and that the premonitory pattern updating unit updates the premonitory pattern on the basis of the detection information detected before either a starting time of the elapsed time or the occurrence time which is input by the operation unit.

Here, when the occurrence time of the abnormality is unknown, an extraction range of a premonitory pattern from detection information detected in the past is widened, which results in not only difficulty in extracting the premonitory pattern but also a tendency for an extraction time to be increased. On the other hand, when the occurrence time of the abnormality can be ascertained, it is possible to narrow the extraction range of the premonitory pattern, which results in not only a tendency for the premonitory pattern to be extracted but also a tendency for the extraction time to be shortened.

For this reason, in the first aspect with the configuration described above, the premonitory pattern updating unit updates a premonitory pattern on the basis of detection information which is detected before either an occurrence time of abnormality or a starting of an elapsed time which is input. Thereby, it is possible to narrow the extraction range compared to a case where the occurrence time of abnormality is unknown. Therefore, it is possible to more accurately extract the premonitory pattern according to the premonitory symptom in a relative short period of time and to update the premonitory pattern to an appropriate premonitory pattern.

In the first aspect, in a state where the abnormality has not occurred in the user, it is preferable that the premonitory symptom determination unit determines that a premonitory symptom has occurred in the user when a pattern based on the detection information detected by the detection unit is similar to the premonitory pattern rather than a normal pattern which is a pattern of the detection information according to the state where the premonitory symptom and the abnormality have not occurred, and determines that the premonitory symptom has not occurred in the user when the pattern is similar to the normal pattern.

Here, when it is determined whether or not the premonitory symptom has occurred by matching of the pattern based on the detection information and the premonitory pattern, a substantial mismatch between these patterns results in a possibility that it is not determined that the premonitory symptom has not occurred, regardless of the occurrence of the premonitory symptom.

On the other hand, in the first aspect with the configuration described above, the premonitory symptom determination unit determines to which one of the premonitory pattern and the normal pattern based on the detection information is similar, and determines that the premonitory symptom has occurred when it is determined that the pattern is similar to the premonitory pattern. Thereby, when the pattern is more similar to the premonitory pattern than the normal pattern even when the pattern based on the detection information and the premonitory pattern do not substantially match each other, it is possible to determine that the premonitory symptom has occurred. Therefore, it is possible to reliably detect and ascertain the occurrence of the premonitory symptom.

In the first aspect, it is preferable that the abnormality prediction device further includes a normal pattern storage unit that stores the normal pattern, an abnormality determination unit that determines whether or not an abnormality has occurred in the user, a period determination unit that determines whether or not a predetermined period of time during which the abnormality determination unit determines that abnormality has not occurred in the user has elapsed, and a normal pattern updating unit that, when the period determination unit determines that the predetermined period of time has elapsed, updates the normal pattern on the basis of the detection information detected by the detection unit during the predetermined period of time.

According to the first aspect with this configuration, the normal pattern stored in the normal pattern storage unit is updated by the normal pattern updating unit on the basis of detection information which is actually detected. Thereby, it is possible to update to a normal pattern according to a state and action of a user. Therefore, it is possible to more accurately determine the occurrence of the premonitory symptom.

Here, in a user's daily life, abnormalities do not frequently occur depending on the type (for example, seizure) of abnormality. On the other hand, in a user's daily life, information detected by the detection unit fluctuates depending on a type of action, and thus the normal pattern is required to be set as an average pattern during a relatively long period of time.

On the other hand, when the period determination unit determines that a predetermined period of time during which the abnormality determination unit determines that abnormality has not occurred has elapsed, the normal pattern is updated on the basis of detection information detected during the predetermined period of time. Thereby, it is possible to suppress the frequent occurrence of a process of updating the normal pattern, and thus the power consumption of the abnormality prediction device can be reduced. Moreover, the normal pattern can be set as an average pattern during a relatively long period of time, and thus it is possible to suppress the updating of a normal pattern used in determining the occurrence of a premonitory symptom to a pattern having a relatively large fluctuation range of detection information. Therefore, it is possible to more appropriately determine the occurrence of the premonitory symptom.

In the first aspect, when it is determined that the abnormality has occurred in the user, it is preferable that the information output unit outputs information indicating the occurrence of the abnormality.

According to the first aspect, not only in a case where it is determined that a premonitory symptom of abnormality has occurred but also in a case where it is determined that abnormality has occurred, information indicating the purport is output. For this reason, the abnormality prediction device or the external device gives notice of the information, and thus it is possible to inform, for example, a user, a person located close to the user, the family of the user, and a medical worker of the occurrence of abnormality.

In the first aspect, it is preferable that the detection unit includes at least one of a biological information detection unit that detects a pulse wave of the user as the biological information and a body motion information detection unit that detects acceleration varying in association with the body motion of the user as the body motion information.

Here, for example, when seizure such as fainting occurs as an abnormality, changes in pulse wave and body motion different from those during the normal time occur.

For this reason, in the first aspect, the detection unit includes at least one of the biological information detection unit that detects a pulse wave and the body motion information detection unit that detects acceleration varying in association with the body motion of the user, and thus it is possible to appropriately determine the occurrence of abnormality and a premonitory symptom.

An abnormality prediction system according to a second aspect of the invention includes a detection device that detects detection information regarding a user and an information processing device that processes detection information detected by the detection device. The detection device includes a detection unit that detects detection information including at least one of biological information of the user and body motion information regarding the body motion of the user, a detection information transmission unit that transmits the detection information to the information processing device, and a notification unit that notifies the user of information received from the information processing device. The information processing device includes a premonitory symptom determination unit that determines whether or not the premonitory symptom has occurred in the user on the basis of the detection information received from the detection device and a premonitory pattern which is a pattern of the detection information according to a premonitory symptom of abnormality occurring in the user, and a notification information transmission unit that, when the premonitory symptom determination unit determines that the premonitory symptom has occurred, transmits notification information indicating that the occurrence of the abnormality in the user is predicted to the detection device.

According to the second aspect, it is possible to exhibit the same effects as in the abnormality prediction device according to the first aspect.

An abnormality prediction method according to a third aspect of the invention is an abnormality prediction method which is performed using a detection device that detects a state of a user. The method includes detecting detection information including at least one of biological information of the user and body motion information regarding the body motion of the user, determining whether or not a premonitory symptom of abnormality has occurred in the user on the basis of the detection information detected and a premonitory pattern which is a pattern of the detection information according to the premonitory symptom of abnormality occurring in the user, and outputting, when it is determined that the premonitory symptom has occurred, notification information indicating the occurrence of abnormality in the user is predicted.

According to the third aspect, the abnormality prediction method is performed using the detection device, and thus it is possible to exhibit the same effects as in the abnormality prediction device according to the first aspect.

A biological information measuring device according to a fourth aspect of the invention includes a biological information detection unit that detects biological information of a user, a body motion information detection unit that detects body motion information of the user, a motion amount calculation unit that calculates a motion amount of the user on the basis of the biological information and the body motion information, a limit value setting unit that sets a limit value of the motion amount according to the user, a notification determination unit that determines a possibility of abnormality occurring in the user on the basis of the calculated motion amount and the set limit value, and a notification unit that gives notice of a warning when the notification determination unit determines that there is an increasing possibility of the abnormality occurring.

According to the fourth aspect, when the notification determination unit determines that there is an increasing possibility of abnormality occurring in a user on the basis of the motion amount and the limit value which are calculated on the basis of the detected biological information and body motion information, respectively, the notification unit gives notice of a warning. Thereby, in a step in which there is an increasing possibility of the abnormality occurring, that is, a step before the abnormality occurs, it is possible to give notice of a warning indicating the purport. Therefore, the user recognizes the warning, and thus it is possible to make it easier to take action for coping with the abnormality. In addition, a monitoring person of a user or a person around the user recognizes the warning, and thus it is possible to provide aid to the user.

In the fourth aspect, it is preferable that the motion amount calculation unit calculates a total value of a motion amount after the user's motion is started and a period motion amount which is a motion amount during a predetermined period of time after the user's motion is started, and that the notification determination unit determines that there is an increasing possibility of the abnormality occurring, on the basis of the period motion amount, at a predetermined time before the total value reaching the limit value.

Meanwhile, the predetermined period of time can be set as a period of time during which a user easily determines a time or a period of time during which the biological information measuring device easily performs a calculation process, and one minute serving as a unit time can be exemplified.

According to the fourth aspect with this configuration, the notification determination unit determines that there is an increasing possibility of abnormality occurring in a user, on the basis of the period motion amount, at a predetermined time before the total value reaches the limit value. The period motion amount is a motion amount during a predetermined period of time. That is, the notification determination unit determines that there is an increasing possibility of the abnormality occurring in the user at a predetermined time before the total value of the motion amount reaches the limit value. Thereby, it is possible to notify a user that there is a high possibility of abnormality occurring while securing a postponement time for the user to perform action with respect to the abnormality.

In the fourth aspect, when a quotient obtained by dividing a residual motion amount, which is obtained by subtracting the total value from the limit value, by the period motion amount becomes the predetermined time or less, it is preferable that the notification determination unit determines that there is an increasing possibility of the abnormality occurring.

According to the fourth aspect, it is possible to appropriately calculate a time between when a motion is started and when a total value of a motion amount reaches a limit value. Accordingly, it is possible to reliably give notice of the warning at a predetermined time prior to a time when the total value reaches the limit value. Therefore, it is possible to reliably notify a user that there is a high possibility of abnormality occurring while reliably securing the postponement time.

In the fourth aspect, it is preferable that the period motion amount is a motion amount during the latest predetermined period of time.

Here, when a user performs a motion, the intensity and pace of the motion are not necessarily fixed. For this reason, in order to accurately ascertain a time when the total value reaches the limit value, it is necessary to calculate a motion amount during a latest predetermined period of time.

On the other hand, in the first aspect with the configuration described above, since the period motion amount is a motion amount during a latest predetermined time, a motion is continued at the present intensity and pace, and thus it is possible to more accurately calculate a time when the total value reaches the limit value. Therefore, it is possible to give notice of the warning at a more appropriate timing.

In the fourth aspect, it is preferable that the motion amount calculation unit calculates a total value of a motion amount after the user's motion is started and that the notification determination unit determines that there is an increasing possibility of the abnormality occurring when the total value has reached a predetermined proportion of the limit value.

According to the fourth aspect, when the total value of the motion amount after the user's motion is started reaches the predetermined proportion of the limit value, the notification determination unit determines that there is an increasing possibility of abnormality occurring, and the notification unit gives notice of a warning. Thereby, as described above, it is possible to notify the user that there is a high possibility of abnormality occurring while securing a time until the total value reaches the limit value, that is, a postponement time for a user to perform action with respect to the abnormality.

In the fourth aspect, it is preferable that the notification determination unit functions at predetermined time intervals.

Here, when a time between when the warning is given notice of and when a user performs action to abnormality is secured, it is considered that it is not necessary to frequently perform a determination process using the notification determination unit and the notification of the warning using the notification unit.

For this reason, according to the fourth aspect, the notification determination unit performs the determination process at predetermined time intervals, and thus it is possible not only to reduce a processing load of the biological information measuring device but also to reduce power consumption.

In the fourth aspect, it is preferable that the limit value includes a first limit value which is set in advance on the basis of the severity of the user's symptom and a second limit value in which motion amounts integrated between when the user's motion is started and when a predetermined input operation is performed are set, and that the notification determination unit determines a possibility of abnormality of the user occurring on the basis of at least one of the calculated motion amount, and the set first limit value and second limit value.

According to the fourth aspect with this configuration, the determination process using the notification determination unit may be performed on the basis of the first limit value or may be performed on the basis of the second limit value. Among these limit values, the first limit value is a limit value which is set in advance on the basis of the severity of the user's symptom. For example, the first limit value is a limit value which is set from a medical viewpoint. The second limit value is motion amounts integrated between when the user's motion is started and when a predetermined input operation is performed by the user. For example, the second limit value is a total value from when the user felt the occurrence of abnormality in the past. For this reason, the determination process is performed on the basis of at least one of the first limit value and the second limit value, and the warning is given notice of according to results of the determination process, and thus it is possible to give notice of the warning in at least one of the same timing from when the user felt abnormality in the past and a timing when it is determined that there is an increasing possibility of abnormality occurring from a medical viewpoint. Therefore, it is possible to reliably notify that there is an increasing possibility of abnormality occurring in the user.

In the fourth aspect, it is preferable that the motion amount calculation unit calculates a latest motion amount which is a motion amount during a latest predetermined period of time after the user's motion is started, and that the notification unit notifies a time based on the quotient, obtained by dividing the limit value by the latest motion amount, as a time when a motion can be performed.

According to the fourth aspect with this configuration, the time is given notice of, and thus it is possible to use the time as a standard time of a motion permissible to the user until reaching the limit value. Therefore, the user can easily ascertain a time until a possibility of abnormality occurring is increased.

In the fourth aspect, it is preferable that the motion amount is an activity amount.

Here, the activity amount (METs) that is set for each type of motion, is a unit indicating the intensity of body activity, and can be calculated on the basis of the body motion information.

For this reason, according to the fourth aspect with the configuration described above, it is possible to more appropriately calculate a motion amount of a user. Therefore, it is possible to reliably notify an increase in the possibility of abnormality occurring in the user.

A biological information measuring system according to a fifth aspect of the invention includes the biological information measuring device and an information processing device that communicates with the biological information measuring device. When the notification determination unit determines that there is an increasing possibility of the abnormality occurring, the information processing device gives notice of predetermined information.

Meanwhile, examples of the predetermined information which is given notice of by the information processing device can include a method of coping with the abnormality and a contact address of a medical institution or the family.

According to the fifth aspect, it is possible to exhibit the same effects as in the biological information measuring device.

In addition, when the notification determination unit of the biological information measuring device determines that a possibility of the abnormality occurring is increasing, the warning is given notice of by the notification unit of the biological information measuring device, and predetermined information is given notice of by the information processing device. Thereby, the information processing device gives notice of, for example, an emergency contact address, and thus a user can easily and rapidly contact the contact address. In addition, the information processing device gives notice of a method of coping with abnormality, and thus the user can perform action shown in the method to thereby avoid the occurrence of abnormality. Therefore, it is possible to improve the versatility and convenience of the biological information measuring system.

A warning notification method according to a sixth aspect of the invention is a warning notification method which is performed using a measurement device that measures biological information and body motion information of a user. The method includes detecting the biological information of the user, detecting the body motion information of the user, calculating a motion amount of the user on the basis of the biological information and the body motion information, determining a possibility of abnormality occurring in the user on the basis of the calculated motion amount and a limit value which is set according to the user, and giving notice of a warning when it is determined that there is an increasing possibility of the abnormality occurring.

According to the sixth aspect, the biological information measuring device performs the warning notification method, and thus it is possible to exhibit the same effects as in the biological information measuring device according to the first aspect.

BRIEF DESCRIPTION OF THE DRAWINGS

The invention will be described with reference to the accompanying drawings, wherein like numbers reference like elements.

DESCRIPTION OF EXEMPLARY EMBODIMENTS

First Embodiment

Figure 1:
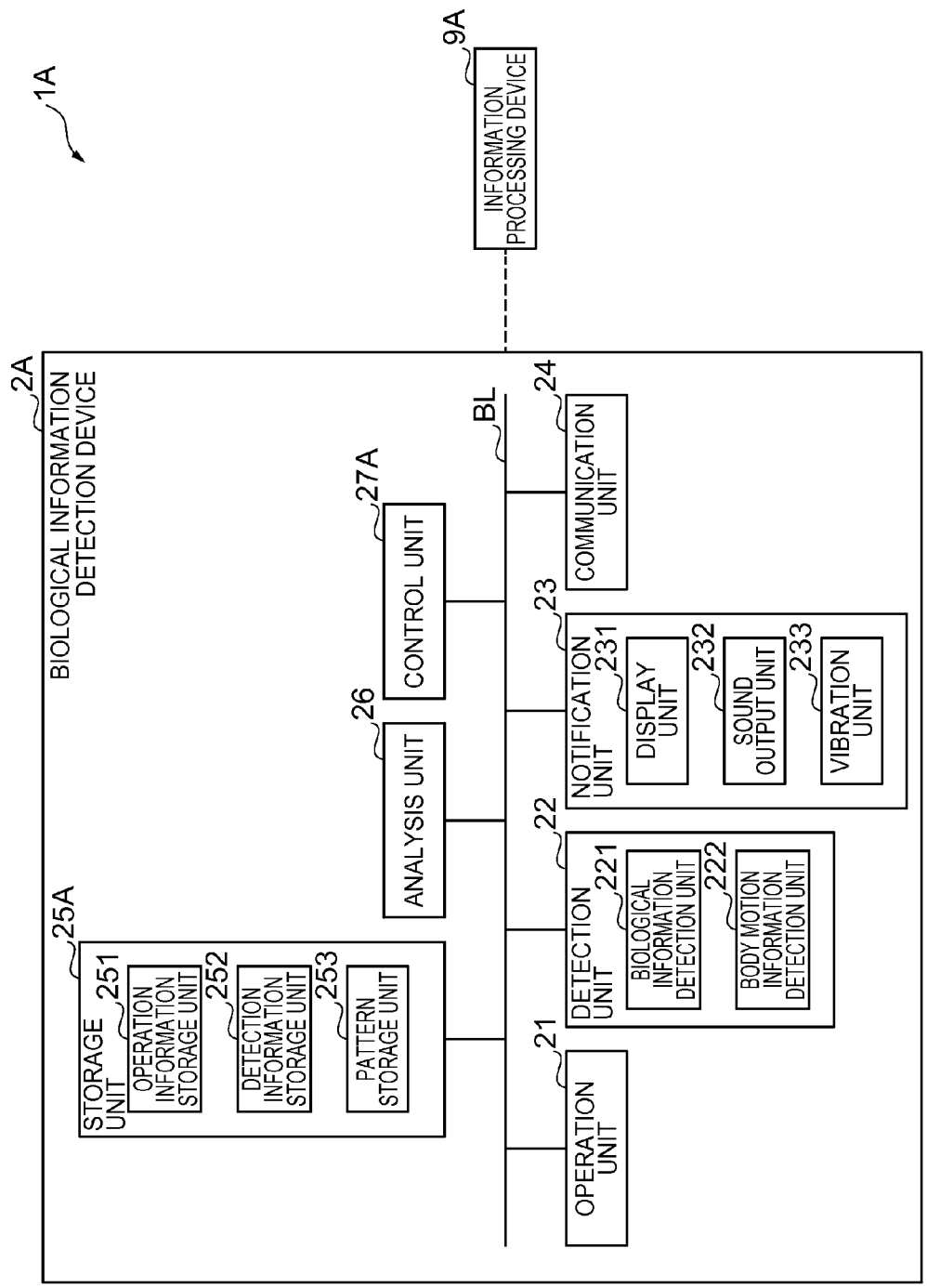
FIG. 1 is a block diagram illustrating a configuration of a biological information measuring system according to a first embodiment of the invention.

Hereinafter, a first embodiment of the invention will be described with reference to the accompanying drawings.
Overall Configuration of Biological Information Measuring System FIG. 1 is a block diagram illustrating a configuration of a biological information measuring system 1A according to this embodiment.

The biological information measuring system 1A according to this embodiment is equivalent to an abnormality prediction system according to the invention, and includes a biological information detection device (hereinafter, may be simply referred to as a detection device) 2A and an information processing device 9A which is capable of communicating with the detection device 2A.

In the biological information measuring system 1A, the detection device 2A detects biological information and operation information of a user wearing the detection device 2A, and notifies the user of a warning when it is determined that a premonitory symptom of abnormality has occurred in the user on the basis of the pieces of information.

In addition, the information processing device 9A acquires various pieces of information detected by the detection device 2A, and uploads the pieces of information and analysis results of the information to a server on a network. Examples of such an information processing device 9A include a personal computer (PC) capable of executing an analysis program of biological information, a smartphone (multi-functional mobile phone), a tablet, and the like.

Here, in the biological information measuring system 1A, as abnormality occurring in the user, the detection device 2A detects seizure such as fainting, epilepsy, and convulsions or seizure accompanied by at least one of impaired consciousness and a movement disorder due to a sudden onset caused by another disease. For this reason, in this embodiment, a nap considered to be included in a sleep may not be included in abnormality occurring in a user.
Configuration of Biological Information Detection Device Hereinafter, a configuration and an operation of the detection device 2A will be described.

The detection device 2A is equivalent to an abnormality prediction device according to the invention, and is a wearable device which is used by being worn on a user. As described above, the detection device 2A detects biological information and body motion information of a user wearing the detection device, and gives notice of a warning when it is determined that a premonitory symptom of abnormality has occurred.

As illustrated in FIG. 1, the detection device 2A includes an operation unit 21, a detection unit 22, a notification unit 23, a communication unit 24, a storage unit 25A, an analysis unit 26, and a control unit 27A which are connected to each other through a bus line BL. Although not shown in FIG. 1, the detection device 2A includes a battery that supplies power to a component.
Configuration of Operation Unit The operation unit 21 includes a plurality of buttons which are provided to be exposed from a case constituting the exterior of the detection device 2A, and outputs an operation signal based on the button input (pressed) to the control unit 27A. For example, when an input operation according to the occurrence of seizure is performed by a user, the operation unit 21 outputs a seizure occurrence signal, which is an operation signal indicating the occurrence of seizure, to the control unit 27A. In addition, the operation unit 21 is configured to be able to input an occurrence time of seizure or an elapsed time since the occurrence of seizure. When the occurrence time or the elapsed time is input, the operation unit outputs an operation signal indicating the occurrence time or the elapsed time to the control unit 27A. Meanwhile, the operation unit 21 is not limited to being configured to include a button, and may be configured to detect a touch panel disposed on a display unit 231 constituting a notification unit 23 to be described later or a user's tap operation and to output an operation signal according to the tap operation to the control unit 27A.
Configuration of Detection Unit The detection unit 22 includes a biological information detection unit 221 that detects biological information of a user and a body motion information detection unit 222 that detects body motion information of a user under the control of the control unit 27A.

The biological information detection unit 221 detects the biological information of the user as a signal, and outputs the detected signal to the analysis unit 26. The biological information detection unit 221 includes a pulse wave sensor that detects a pulse wave of a user, a brain wave sensor that detects a brain wave, an electrocardiographic sensor that detects electrical activity in the heart, and a temperature sensor that detects body temperature.

Among these, the pulse wave sensor can be constituted by a light emitting element such as, for example, a light emitting diode (LED), and a photoelectric sensor including a light receiving element such as a photodiode.

In addition, the brain wave sensor can be constituted by, for example, a headset type sensor which is worn on a user's head. In this case, the brain wave sensor can be configured to output a brain wave detected in a wireless or wired manner and to output the brain wave from the detection unit 22 to the analysis unit 26.

The body motion information detection unit 222 detects body motion information of a user. The body motion information detection unit 222 includes an acceleration sensor that detects acceleration varying in association with the body motion of the user as the body motion information and outputs an acceleration signal indicating the detected acceleration to the control unit 27A. Examples of such an acceleration sensor can include a three-axis sensor that detects acceleration at each of X, Y and Z axes. Meanwhile, an acceleration signal which is a detection result of the acceleration sensor can be used for a process of reducing noise caused by a body motion which is superimposed on a pulse wave signal detected by the pulse wave sensor.

Configuration of Notification Unit

The notification unit 23 notifies a user of various pieces of information under the control of the control unit 27A. The notification unit 23 includes a display unit 231, a sound output unit 232, and a vibration unit 233.

The display unit 231 is constituted by any of various types of display panels such as liquid crystal, a plurality of LEDs, or the like, and displays contents based on notification information which is input from the control unit 27A. For example, the display unit 231 displays biological information and operation information which are detected by the detection unit 22 and are analyzed by the analysis unit 26. In addition, when it is determined in a prediction determination process to be described later that a premonitory symptom of abnormality has occurred in a user, the display unit 231 displays a message indicating that there is a high possibility of abnormality occurring in a short period of time in the future.

The sound output unit 232 is configured to include a sound output section such as a speaker, and outputs a sound based on sound information which is input from the control unit 27A. For example, when it is determined in a prediction determination process to be described later that a premonitory symptom of abnormality has occurred in a user, the sound output unit 232 outputs a warning sound.

The vibration unit 233 includes a motor of which the operation is controlled by the control unit 27A, and notifies a user of, for example, a warning by vibration generated by the driving of the motor.

Configuration of Communication Unit

The communication unit 24 includes a communication module capable of communicating with an external device such as the information processing device 9A. The communication unit 24 transmits information stored in the storage unit 25A to, for example, an external device in response to a request signal which is received from the external device. Meanwhile, in this embodiment, the communication unit 24 communicates with an external device in a wireless manner, but may communicate with the external device through a relay device such as a cradle, or may communicate with the external device through a cable when the detection device 2A and the external device are connected to each other through the cable.

Configuration of Storage Unit

The storage unit 25A is constituted by a storage device including a flash memory or the like, and includes an operation information storage unit 251, a detection information storage unit 252, and a pattern storage unit 253.

The operation information storage unit 251 stores various types of programs necessary for an operation of the detection device 2A and operation information such as data. As such an operation information, the operation information storage unit 251 stores a control program for controlling an operation of the detection device 2A and respective programs for independently executing an updating process and a prediction determination process which are included in an abnormality prediction process to be described later.

The detection information storage unit 252 stores pieces of detection information including biological information and body motion information detected by the detection unit 22 and analysis results of the analysis unit 26 to be described later. The detection information storage unit 252 is configured to sequentially store the pieces of detection information and to overwrite information first stored with information, which is newly acquired, in the case of an insufficient storage capacity.

The pattern storage unit 253 is equivalent to a premonitory pattern storage unit and a normal pattern storage unit according to the invention. The pattern storage unit 253 stores state identification patterns including a seizure pattern, a premonitory pattern, and a normal pattern which are used in an abnormality prediction process to be described later. These state identification patterns include an aging pattern of a signal waveform of each of the biological information and the operation information which are detected by the detection unit 22, an aging pattern of a parameter which is obtained by analyzing these pieces of information, and appearance patterns (a case where pieces of the same information or pieces of different information appear with a time difference is included) of these aging patterns.

Among the state identification patterns, the seizure pattern is a pattern in a case where seizure occurs in a user, and the premonitory pattern is a pattern in a case where a premonitory symptom of the seizure occurs. In addition, the normal pattern is a pattern in a case where seizure or a premonitory symptom of the seizure have not occurred in a user. The state identification patterns are updated at any time by the control unit 27A to be described later.

Configuration of Analysis Unit

The analysis unit 26 includes a signal processing circuit such as a digital signal processor (DSP), and analyzes various pieces of information detected by the detection unit 22 as signals to thereby calculate various types of parameters.

For example, the analysis unit 26 calculates the number of pulses, an estimated blood flow rate, and a pulse variation per unit time on the basis of the pulse wave signal detected by the pulse wave sensor, performs spectrum analysis on the pulse wave signal, and obtains a low frequency (LF)/high frequency (HF) value as an index indicating a balance between sympathetic nerve activity and parasympathetic nerve activity.

Meanwhile, HF has a cycle of approximately 3 seconds to 4 seconds, and indicates a fluctuation wave using a breath as a signal source or a total amount of a power spectrum of the frequency region thereof. On the other hand, LF indicates a fluctuation wave, referred to as a mayer wave, using a change in blood pressure having a cycle of approximately 10 seconds as a signal source or a total amount of a power spectrum of the frequency region thereof.

In addition, the analysis unit 26 performs frequency analysis of a brain wave signal detected by the brain wave sensor. Further, the analysis unit 26 calculates a contraction interval of the heart and the number of times of extrasystole per unit time, and calculates user's body temperature on the basis of detection results of the temperature sensor. In addition, the analysis unit 26 calculates a user's motion amount and motion spectrum per unit time on the basis of an acceleration signal detected by the body motion information detection unit 222.

Such analysis of the analysis unit 26 is performed with a predetermined cycle, and biological information and body motion information detected during the cycle are analyzed. Analysis results of the analysis unit 26, that is, calculated various types of parameters are stored in the detection information storage unit 252 as detection information together with the biological information, the body motion information, and a detection time of a signal used for the calculation of the various types of parameters.

Meanwhile, parameters to be calculated by the analysis unit 26 are not limited to the above-mentioned parameters. That is, the analysis unit 26 may calculate other parameters instead of or in addition to the above-mentioned parameters.

Configuration of Control Unit

Figure 2:
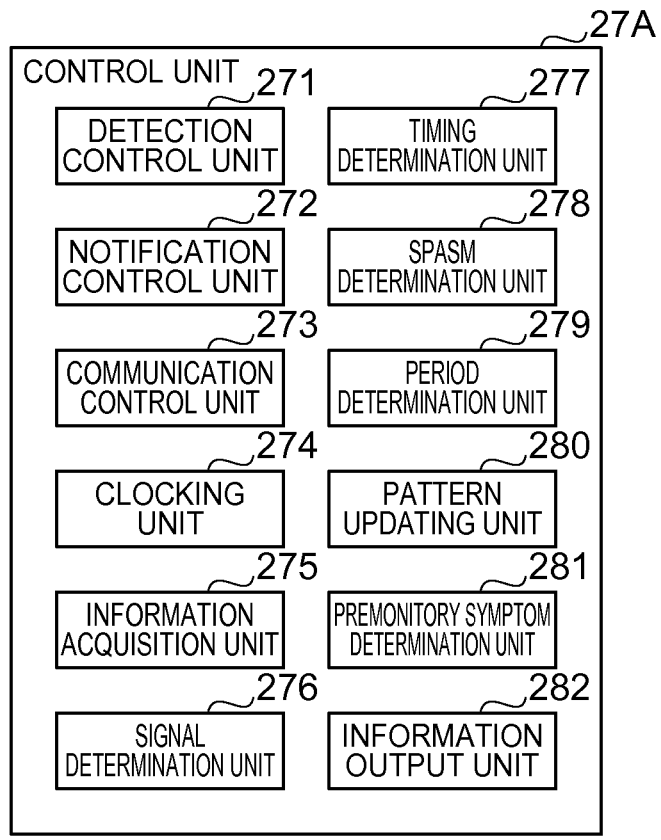
FIG. 2 is a block diagram illustrating a configuration of a control unit of a biological information detection device according to the first embodiment.

FIG. 2 is a block diagram illustrating a configuration of the control unit 27A.

The control unit 27A includes a processing circuit such as a central processing unit (CPU), and controls an operation of the detection device 2A autonomously or in response to an operation signal which is input from the operation unit 21. For example, the control unit 27A performs an abnormality prediction process to be described later, updates the state identification pattern on the basis of the analysis results of the analysis unit 26, and gives notice of a warning when it is determined that a premonitory symptom of seizure has occurred and it is determined that seizure has occurred.

In order to perform such a process, the control unit 27A includes a detection control unit 271, a notification control unit 272, a communication control unit 273, a clocking unit 274, an information acquisition unit 275, a signal determination unit 276, a timing determination unit 277, a seizure determination unit 278, a period determination unit 279, a pattern updating unit 280, a premonitory symptom determination unit 281, and an information output unit 282, as illustrated in FIG. 2, as functional units realized by the processing circuit executing programs stored in the operation information storage unit 251.

The detection control unit 271 controls an operation of the detection unit 22, and stores detection results of the detection unit 22 in the detection information storage unit 252 together with a time (detection time) at the present date and time which is clocked by the clocking unit 274 to be described later.

The notification control unit 272 controls an operation of the notification unit 23. For example, the notification control unit 272 outputs an operation state of the detection device 2A and notification information including a display and a sound which indicate detection results of the detection unit 22 and the like to the notification unit 23 to thereby notify the notification unit 23 of the notification information. In addition, the notification control unit 272 drives a motor of the vibration unit 233 as necessary and gives notice of predetermined information by vibration generated by the driving of the motor.

The communication control unit 273 controls an operation of the communication unit 24 that communicates with the external device.

The clocking unit 274 clocks the present date and time.

The information acquisition unit 275 functions at the time of the execution of processes included in an abnormality prediction process to be described later, and acquires detection information stored in the detection information storage unit 252.

The signal determination unit 276, the timing determination unit 277, the seizure determination unit 278, the period determination unit 279, and the pattern updating unit 280 function at the time of the execution of an updating process included in the abnormality prediction process.

Among these, the signal determination unit 276 determines whether or not the seizure occurrence signal indicating the occurrence of seizure is input from the operation unit 21.

The timing determination unit 277 determines whether a timing when the occurrence of seizure based on up-to-date detection information is determined is set.

The seizure determination unit 278 is equivalent to an abnormality determination unit. The seizure determination unit 278 determines whether seizure has occurred in a user on the basis of detection information acquired during an up-to-date cycle by the information acquisition unit 275 operating with a predetermined cycle and the seizure pattern and the normal pattern which are stored in the pattern storage unit 253. For example, the seizure determination unit 278 determines that a change in a parameter which corresponds to the seizure pattern and the normal pattern and which is included in the acquired detection information is similar to which one of the seizure pattern and the normal pattern. The seizure determination unit 278 determines that seizure has occurred in a user when the seizure determination unit determines that the changes in parameter are similar to the seizure pattern, the seizure determination unit determines that seizure has not occurred in a user when the seizure determination unit determines that the changes in parameter are similar to the normal pattern.

The period determination unit 279 determines whether a predetermined period of time during which the seizure occurrence signal has not been input and a predetermined period of time during which it is not determined that seizure has occurred have elapsed. That is, the period determination unit 279 determines whether a predetermined period of time during which seizure has not occurred has elapsed.

The pattern updating unit 280 is equivalent to a premonitory pattern updating unit according to the invention. The pattern updating unit 280 functions in a case where the signal determination unit 276 determines that the seizure occurrence signal has been input and a case where the seizure determination unit 278 determines that seizure has occurred. The pattern updating unit 280 extracts the premonitory pattern on the basis of detection information which is detected and analyzed before a seizure occurrence timing, and updates the premonitory pattern stored in the pattern storage unit 253.

In addition, the pattern updating unit 280 extracts the seizure pattern on the basis of detection information which is detected and analyzed after the seizure occurrence timing, and similarly updates the seizure pattern stored in the pattern storage unit 253.

Meanwhile, when an operation signal indicating the seizure occurrence timing is input together with the seizure occurrence signal in a case where it is determined that the seizure occurrence signal has been input, the pattern updating unit 280 specifies the seizure occurrence timing on the basis of an occurrence timing indicated by the operation signal, and updates a premonitory pattern and a seizure pattern on the basis of detection information which is detected and analyzed before and after the occurrence timing.

Further, the pattern updating unit 280 is equivalent to a normal pattern updating unit according to the invention. When the period determination unit 279 determines that a predetermined period of time during which seizure has not occurred has elapsed, the pattern updating unit extracts the normal pattern on the basis of detection information which is detected and analyzed during the predetermined period of time and updates the normal pattern stored in the pattern storage unit 253.

When each pattern is updated by the pattern updating unit 280, the state identification patterns stored in the pattern storage unit 253 may be updated by the extracted state identification patterns (seizure pattern, a premonitory pattern, and a normal pattern). Thereby, it is possible to construct the state identification patterns based on user's actual detection information.

However, considering the accuracy of the state identification patterns, it is preferable that the state identification patterns stored in the pattern storage unit 253 are updated by an average pattern of each of the extracted state identification patterns.

For example, it is considered that the premonitory pattern stored in the pattern storage unit 253 is updated by an average pattern between a premonitory pattern newly extracted and a premonitory pattern extracted in the past.

In addition, for example, it is considered that a premonitory pattern including the premonitory pattern newly extracted and the premonitory pattern extracted in the past is generated and that the stored premonitory pattern is updated by the generated premonitory pattern.

Further, for example, it is considered that only a matching pattern in the premonitory pattern newly extracted and the premonitory pattern extracted in the past is generated as a new premonitory pattern and that the stored premonitory pattern is updated by the new premonitory pattern.

The premonitory symptom determination unit 281 and the information output unit 282 function in a prediction determination process included in the abnormality prediction process.

The premonitory symptom determination unit 281 determines whether or not a premonitory symptom of seizure has occurred in a user on the basis of up-to-date detection information (detection information acquired within one latest cycle) which is acquired with a predetermined cycle by the information acquisition unit 275. Specifically, the premonitory symptom determination unit 281 compares a pattern based on the up-to-date detection information with the premonitory pattern and the normal pattern which are stored in the pattern storage unit 253. Specifically, the premonitory symptom determination unit 281 determines that a premonitory symptom of seizure has occurred when it is determined that an aging pattern of the parameter included in the up-to-date detection information is more similar to the premonitory pattern than the normal pattern, and determines that a premonitory symptom of seizure has not occurred when it is determined that the aging pattern is more similar to the normal pattern than the premonitory pattern.

When the premonitory symptom determination unit 281 determines that a premonitory symptom of seizure has occurred, the information output unit 282 outputs notification information which the notification unit 23 is notified of. Specifically, the information output unit 282 outputs display information, including a message indicating that a premonitory symptom of seizure has occurred and there is a high possibility of seizure occurring in a short period of time in the future, to the display unit 231 of the notification unit 23, and displays the message thereon. In addition, the information output unit 282 causes the sound output unit 232 of the notification unit 23 to output a sound according to the message or a warning sound, drives a motor constituting the vibration unit 233 of the notification unit 23, and gives notice of a warning by vibration generated.

In addition, when the seizure determination unit 278 determines that seizure has occurred in a user, the information output unit 282 outputs notification information including a message indicating that seizure has occurred to the display unit 231, and displays the message thereon. In addition, the information output unit 282 causes the sound output unit 232 to output a predetermined sound and causes the vibration unit 233 to generate vibration.

Meanwhile, these pieces of notification information may be transmitted to an external device (for example, the information processing device 9A) through the communication unit 24.

Abnormality Prediction Process

The detection device 2A performs an abnormality prediction process according to a program stored in the operation information storage unit 251. The abnormality prediction process includes an updating process and a prediction determination process which are described below.

Updating Process

Figure 3:
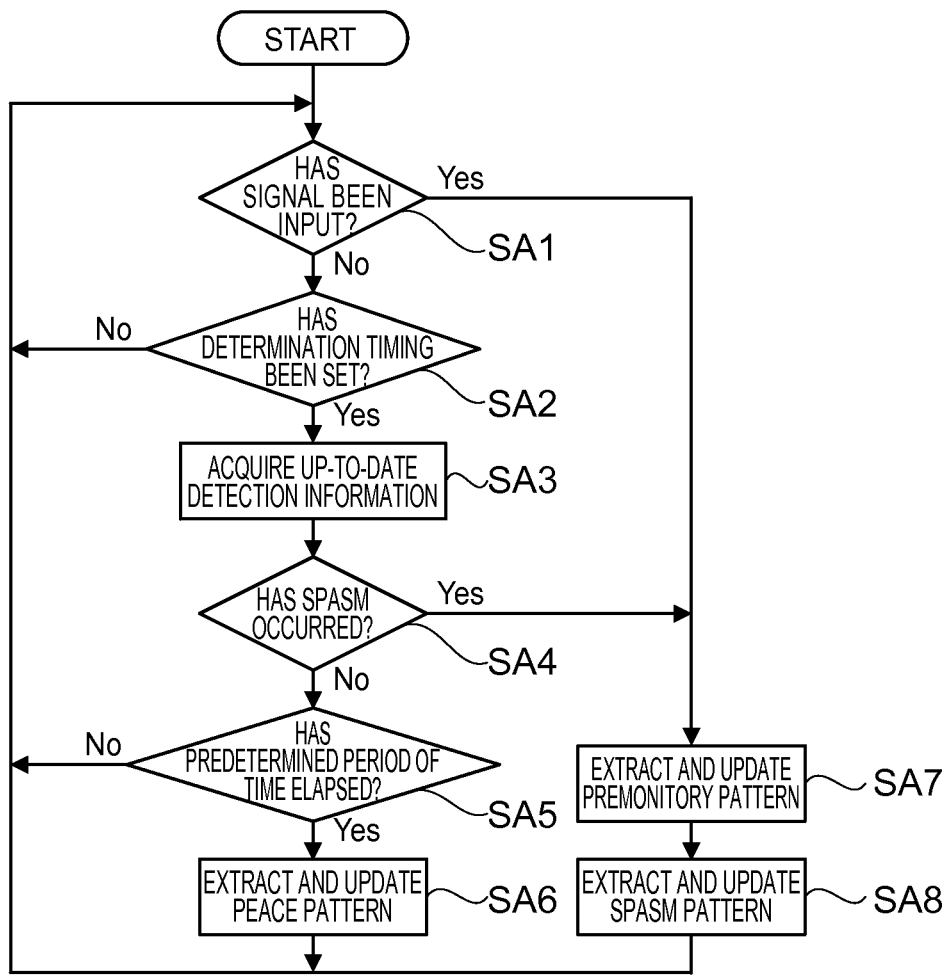
FIG. 3 is a flow chart illustrating an updating process according to the first embodiment.

FIG. 3 is a flow chart illustrating an updating process.

The updating process is a process of updating state identification patterns (seizure pattern, a premonitory pattern, and a normal pattern) which are stored in the pattern storage unit 253, and is repeatedly performed by the control unit 27A.

As illustrated in FIG. 3, in the updating process, first, the signal determination unit 276 determines whether the seizure occurrence signal has been input from the operation unit 21 (step SA1).

Here, when it is determined that the seizure occurrence signal has been input, the control unit 27A shifts the process to step SA7 to be described later.

On the other hand, when it is determined that the seizure occurrence signal has not been input, the timing determination unit 277 determines whether a determination timing when the occurrence of seizure is determined has been set (step SA2). In the determination process of step SA2, it is determined whether or not a sufficient period of time has elapsed after occurrence determination (occurrence determination in step SA4 to be described later) of the previous seizure and detection information sufficient for performing the occurrence determination has been stored. Meanwhile, this occurrence timing is postponed when it is determined in the determination process of step SA1 that the seizure occurrence signal has been input.

When it is determined in the determination process of step SA2 that a determination timing has not been set, the control unit 27A returns the process to step SA1.

On the other hand, when it is determined in the determination process of step SA2 that a determination timing has been set, the information acquisition unit 275 acquires up-to-date detection information (detection information which is detected and analyzed within one latest cycle) (step SA3).

The seizure determination unit 278 determines whether or not seizure has occurred in a user as described above on the basis of a pattern based on the acquired up-to-date detection information and the seizure pattern stored in the pattern storage unit 253 (step SA4).

When it is determined in the determination process of step SA4 that seizure has occurred, the information output unit 282 outputs notification information indicating that seizure has occurred to the notification unit 23 and gives notice of the notification information, and the control unit 27A shifts the process to step SA7 to be described later.

When it is determined in the determination process of step SA4 that seizure has not occurred, the period determination unit 279 determines whether a predetermined period of time during which it is determined that seizure has not occurred has elapsed (step SA5).

Here, when it is determined that the predetermined period of time has not elapsed, the control unit 27A returns the process to step SA1.

On the other hand, when it is determined that the predetermined period of time has elapsed, the pattern updating unit 280 extracts a normal pattern based on detection information which is detected and analyzed during the predetermined period of time. As described above, the pattern updating unit 280 updates the normal pattern stored in the pattern storage unit 253 on the basis of the extracted normal pattern (step SA6).

After step SA6 is performed, the control unit 27A returns the process to step SA1.

In step SA7, the pattern updating unit 280 extracts a premonitory pattern based on the detection information which is detected and analyzed before the seizure occurrence timing (timing when the seizure occurrence signal is input or a timing when it is determined that seizure has occurred). As described above, the pattern updating unit 280 updates the premonitory pattern stored in the pattern storage unit 253 on the basis of the extracted premonitory pattern (step SA7).

Meanwhile, when the operation signal indicating an occurrence time of seizure or an elapsed time since the occurrence of seizure is input together with the seizure occurrence signal, a seizure occurrence timing is specified on the basis of the occurrence time or the elapsed time as described above. The detection information which is detected and analyzed before the occurrence timing is acquired by the information acquisition unit 275, and the stored premonitory pattern is updated by the pattern updating unit 280 on the basis of the detection information.

Further, the pattern updating unit 280 extracts a seizure pattern based on detection information which is detected and analyzed after the seizure occurrence timing, and updates the seizure pattern stored in the pattern storage unit 253 on the basis of the extracted seizure pattern (step SA8). Here, step SA7 and step SA8 may be performed in reverse order or may be performed at the same time.

After step SA7 and step SA8 are performed, the control unit 27A returns the process to step SA1.

In this manner, although one cycle of the updating process is terminated, the updating process may be repeatedly performed by the control unit 27A as described above.

Meanwhile, in step SA6, step SA7, and step SA8 mentioned above, a description has been given that each pattern is extracted and updated on the basis of the detected detection information. However, the invention is not limited thereto, and the pattern updating unit 280 may add the pattern which is detected and extracted (acquired pattern) as a new pattern, as at least one of the normal pattern, the premonitory pattern, and the seizure pattern. For example, when the degree of correlation of the acquired pattern with respect to an existing pattern stored, which is at least one of a normal state (state where abnormality has not occurred), a premonitory state (state where a premonitory symptom has occurred), and an abnormal state (state where abnormality has occurred) has a predetermined value or less, the pattern updating unit 280 functions as a state determination condition addition unit, and may add the acquired pattern to the pattern storage unit 253 as a new pattern without overwriting the existing pattern. Here, the degree of correlation includes a peak intensity ratio of each of a pulse wave signal and an acceleration signal, an integrated value ratio during a predetermined period of time of each of the signals, the degree of matching of a waveform shape of the pulse wave signal, and the like. With such a configuration, it is possible to add and learn a normal pattern, a premonitory pattern, or a seizure pattern depending on a user. Therefore, the state of the user is determined with reference to not only the existing pattern but also the added new pattern, and thus it is possible to more appropriately determine the state of the user which cannot be detected using only the existing pattern and to further improve the detection accuracy of each of the states. In addition, each of the patterns may be updated using another method.

In this embodiment, a configuration has been adopted in which a user performs an input operation on the operation unit 21 to notify the detection device 2A of the occurrence of the seizure and the control unit 27A includes the signal determination unit 276, the timing determination unit 277, and the seizure determination unit 278 on the assumption that the detection device 2A automatically detects the occurrence of seizure. However, the invention is not limited thereto, and the control unit 27A can update a seizure pattern, a premonitory pattern, and a normal pattern even when the control unit is configured to include either the signal determination unit 276 or the timing determination unit 277 and the seizure determination unit 278.

For example, in a configuration in which the control unit 27A includes the signal determination unit 276, step SA2 to step SA4 in the updating process may be omitted. In addition, in a configuration in which the control unit 27A includes the timing determination unit 277 and the seizure determination unit 278, step SA1 in the updating process may be omitted.

Prediction Determination Process

Figure 4:
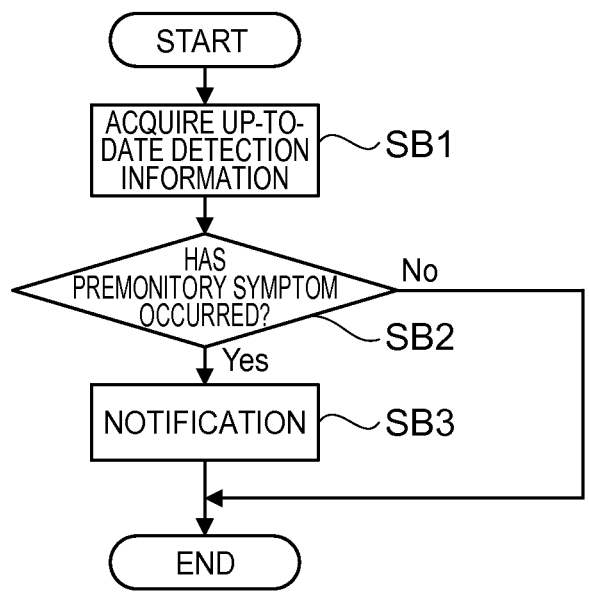
FIG. 4 is a flow chart illustrating a prediction determination process according to the first embodiment.

FIG. 4 is a flow chart illustrating a prediction determination process.

The prediction determination process is a process in which it is determined whether a premonitory symptom of seizure has occurred in a user with a predetermined cycle and the user is notified of a warning when it is determined that the premonitory symptom has occurred.

As illustrated in FIG. 4, in the prediction determination process, first, the information acquisition unit 275 acquires up-to-date detection information in the same manner as in step SA3 mentioned above (step SB1).

Thereafter, the premonitory symptom determination unit 281 determines whether a premonitory symptom of seizure has occurred in a user as described above on the basis of a pattern based on the acquired up-to-date detection information and the premonitory pattern and the normal pattern which are stored in the pattern storage unit 253 (step SB2).

When it is determined in the determination process of step SB2 that a premonitory symptom has not occurred, the control unit 27A terminates the prediction determination process and prepares for the subsequent execution of the prediction determination process.

On the other hand, when it is determined in the determination process of step SB2 that a premonitory symptom has occurred, the information output unit 282 outputs notification information to give notice of a warning (step SB3). By this process, the message is displayed on the display unit 231, a warning is output by the sound output unit 232, and the vibration unit 233 is driven.

In this manner, the prediction determination process is terminated.

Effects of First Embodiment

According to the biological information measuring system 1A described above of this embodiment, the following effects can be exhibited.

The premonitory symptom determination unit 281 determines whether a premonitory symptom of seizure has occurred on the basis of a pattern based on up-to-date detection information detected by the detection unit 22 and a premonitory pattern according to the premonitory symptom of seizure. When it is determined that the premonitory symptom has occurred, the information output unit 282 outputs notification information indicating that there is a high possibility of seizure occurring in a short period of time in the future. Thereby, it is possible to output the notification information in a step before seizure occurs in the user. Therefore, the notification unit 23 gives notice of the notification information, and thus it is possible to inform the user that the occurrence of seizure is predicted. Therefore, the user can take a preliminary countermeasure such as action of avoiding of danger accompanied by the occurrence of seizure.

The detection device 2A which is used by being worn on a user includes the notification unit 23 that notifies the user of the notification information. Thereby, when the occurrence of seizure is predicted, it is possible to rapidly and reliably notify the user of the purport. Therefore, the user can reliably take the preliminary countermeasure.

A premonitory pattern serving as an index indicating whether a premonitory symptom of seizure has occurred in a user is updated by the pattern updating unit 280 on the basis of detection information which is detected before the seizure occurrence timing having occurred in the user. Thereby, it is possible to update the premonitory pattern on the basis of detection information which is actually detected. Therefore, it is possible to more accurately determine whether a premonitory symptom of seizure has occurred in a user.

When the seizure determination unit 278 determines that seizure has occurred, there is a high possibility of a premonitory symptom of the seizure has occurred. For this reason, when the seizure determination unit 278 determines that seizure has occurred, since the pattern updating unit 280 updates the premonitory pattern, it is possible to make it easier to extract the premonitory pattern according to the premonitory symptom from the detection information. Therefore, it is possible to automatically store an appropriate pattern according to the premonitory symptom as a premonitory pattern.

When the signal determination unit 276 determines that the seizure occurrence signal has been input from the operation unit 21 according to a user's input operation, the pattern updating unit 280 updates the premonitory pattern. Thereby, the control unit 27A of the detection device 2A can reliably ascertain that seizure has occurred in the user. Therefore, the premonitory pattern can be updated on the basis of detection information which is actually detected before the seizure occurrence signal is input, and thus it is possible to store a more appropriate premonitory pattern.

Here, when a seizure occurrence timing is unknown, an extraction range of a premonitory pattern from detection information detected in the past is widened, which results in not only a difficulty in extracting the premonitory pattern from the detection information but also an increase in time required for an extraction process. On the other hand, when the control unit 27A can ascertain the seizure occurrence timing, it is possible to narrow the extraction range, which results in not only a tendency for the premonitory pattern to be extracted but also a reduction in time required for the extraction process.

For this reason, the operation unit 21 is configured to be able to input an occurrence time of seizure or an elapsed time since the occurrence of seizure. When the occurrence time or the elapsed time is input by a user, the operation unit transmits an operation signal including either of them to the control unit 27A. The pattern updating unit 280 updates a premonitory pattern on the basis of detection information detected before starting times of the occurrence time and the elapsed time indicated by the operation signal. Thereby, it is possible to narrow the extraction range compared to a case where an occurrence time of abnormality is unknown. Therefore, it is possible to more accurately extract the premonitory pattern in a relative short period of time and to update to the appropriate premonitory pattern.

In determining the occurrence of a premonitory symptom, when it is not determined that the premonitory symptom has occurred due to a substantial mismatch between the pattern based on the detection information and the premonitory pattern, there is a possibility that it is not possible to appropriately determine the occurrence of the premonitory symptom.

On the other hand, the premonitory symptom determination unit 281 determines which one of the premonitory pattern and the normal pattern the pattern based on the detection information is similar to. When it is determined that the pattern is similar to the premonitory pattern, it is determined that the premonitory symptom has occurred. Thereby, when the pattern is more similar to the premonitory pattern than the normal pattern even in a case where the pattern based on the detection information and the premonitory pattern do not substantially match each other, it can be determined that the premonitory symptom has occurred. Therefore, it is possible to reliably detect and ascertain the occurrence of the premonitory symptom.

The pattern updating unit 280 updates the normal pattern stored in the pattern storage unit 253 on the basis of the detection information which is actually detected by the detection unit 22. Thereby, it is possible to perform updating to a normal pattern according to a state and action of a user. Therefore, it is possible to more accurately determine the occurrence of the premonitory symptom.

Here, in user's daily life, seizure does not frequently occur. On the other hand, in the user's daily life, biological information and body motion information which are detected by the detection unit 22 fluctuate depending on a type of action, and thus the normal pattern is required to be set as an average pattern in a relatively long cycle.

On the other hand, when the period determination unit 279 determines that a predetermined period of time during which the seizure determination unit 278 determines that seizure has not occurred has elapsed, the pattern updating unit 280 updates the normal pattern on the basis of detection information detected during the predetermined period of time. Thereby, it is possible to suppress the frequent occurrence of a process of updating the normal pattern, and thus the power consumption of the detection device 2A can be reduced. In addition, since the normal pattern can be set as an average pattern in a relatively long cycle, it is possible to suppress the updating of a normal pattern used in determining the occurrence of a premonitory symptom to a pattern having a relatively large fluctuation range of detection information. Therefore, it is possible to more appropriately determine the occurrence of the premonitory symptom.

The information output unit 282 outputs notification information not only in a case where the premonitory symptom determination unit 281 determines that a premonitory symptom has occurred but also in a case where the seizure determination unit 278 determines that seizure has occurred. For this reason, the notification unit 23 gives notice of the notification information, and thus it is possible to inform a user, a person located close to the user, a family of the user, and a medical worker of the occurrence of seizure.

When seizure occurs as abnormality, changes in pulse wave and body motion different from those during the normal time occur. For this reason, the detection unit 22 includes the biological information detection unit 221 that detects a pulse wave and the body motion information detection unit 222 that detects acceleration varying in association with the body motion of a user, and the analysis unit 26 analyzes signals of the pulse wave and the acceleration which are detected, and thus the control unit 27A can appropriately determine the occurrence of seizure and a premonitory symptom.

Second Embodiment

Next, a second embodiment of the invention will be described.

A biological information measuring system according to this embodiment has the same configuration as the biological information measuring system 1A, but is different from the biological information measuring system 1A in that an information processing device has a portion of functions of an analysis unit that analyzes information detected by the detection unit 22 and a control unit that determines the occurrence of abnormality and a premonitory symptom. Meanwhile, in the following description, components that are the same as or substantially the same as the components that have been described already will be denoted by the same reference numerals and signs, and a description thereof will be omitted here.

Figure 5:
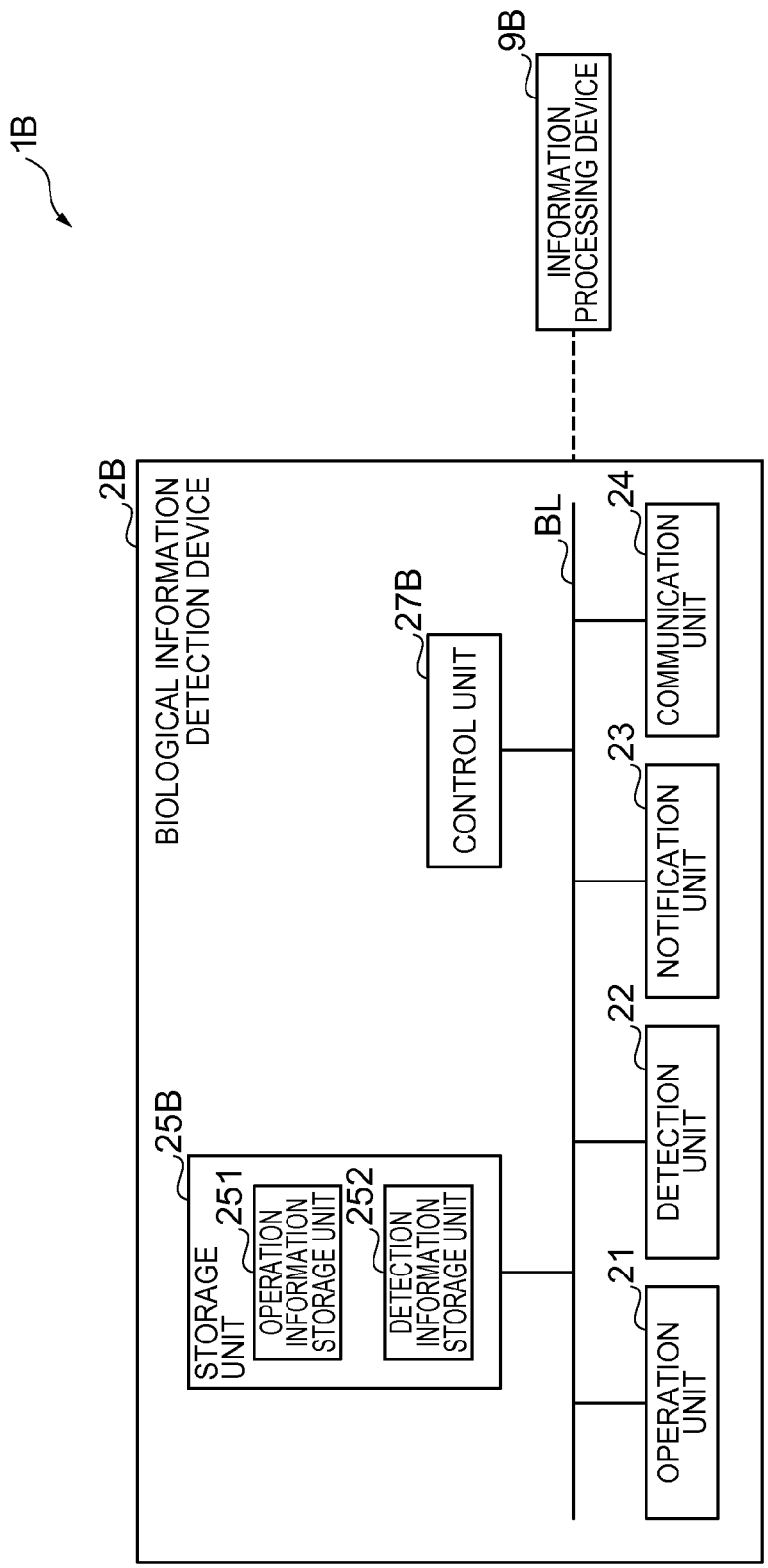
FIG. 5 is a block diagram illustrating a configuration of a biological information measuring system according to a second embodiment of the invention.

FIG. 5 is a block diagram illustrating a configuration of a biological information measuring system 1B according to this embodiment.

The biological information measuring system 1B according to this embodiment is equivalent to an abnormality prediction system according to the invention. As illustrated in FIG. 5, the biological information measuring system 1B includes a biological information detection device 2B and an information processing device 9B, and has the same function as the biological information measuring system 1A.

Configuration of Biological Information Detection Device

A detection device 2B is configured to be able to communicate with an information processing device 9B at all times, and transmits biological information and body motion information detected to the information processing device 9B. In addition, when the information processing device 9B determines that the above-mentioned premonitory symptom has occurred and transmits notification information, the detection device 2B receives the notification information and notifies a user of the notification information. The detection device 2B includes an operation unit 21, a detection unit 22, a notification unit 23, a communication unit 24, a storage unit 25B, and a control unit 27B. That is, the detection device 2B includes the storage unit 25B and the control unit 27B instead of the storage unit 25A and the control unit 27A, and does not include an analysis unit 26.

Among these, the storage unit 25B includes an operation information storage unit 251 and a detection information storage unit 252, but does not include a pattern storage unit 253.

Figure 6:
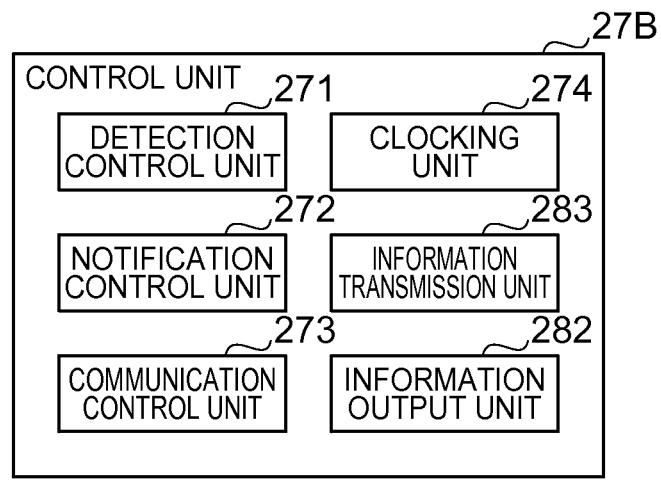
FIG. 6 is a block diagram illustrating a configuration of a control unit of a biological information detection device according to the second embodiment.

FIG. 6 is a block diagram illustrating a configuration of the control unit 27B.

Similarly to the control unit 27A, the control unit 27B controls an operation of the detection device 2B autonomously or according to a user's input operation. As illustrated in FIG. 6, the control unit 27B includes a detection control unit 271, a notification control unit 272, a communication control unit 273, a clocking unit 274, an information transmission unit 283, and an information output unit 282.

The information transmission unit 283 is equivalent to a detection information transmission unit according to the invention, and transmits biological information and operation information which are pieces of detection information, detected by the detection unit 22 and stored in the detection information storage unit 252, to the information processing device 9B with a predetermined cycle. In addition, when the above-mentioned seizure occurrence signal is input from the operation unit 21, the information transmission unit 283 immediately transmits seizure occurrence information including contents of the seizure occurrence signal to the information processing device 9B.

When notification information is received from the information processing device 9B by the communication unit 24, the information output unit 282 outputs the notification information to the notification unit 23 to display the above-mentioned message on a display unit 231, outputs a warning sound using the sound output unit 232, and generates vibration using the vibration unit 233.

Configuration of Information Processing Device

Figure 7:
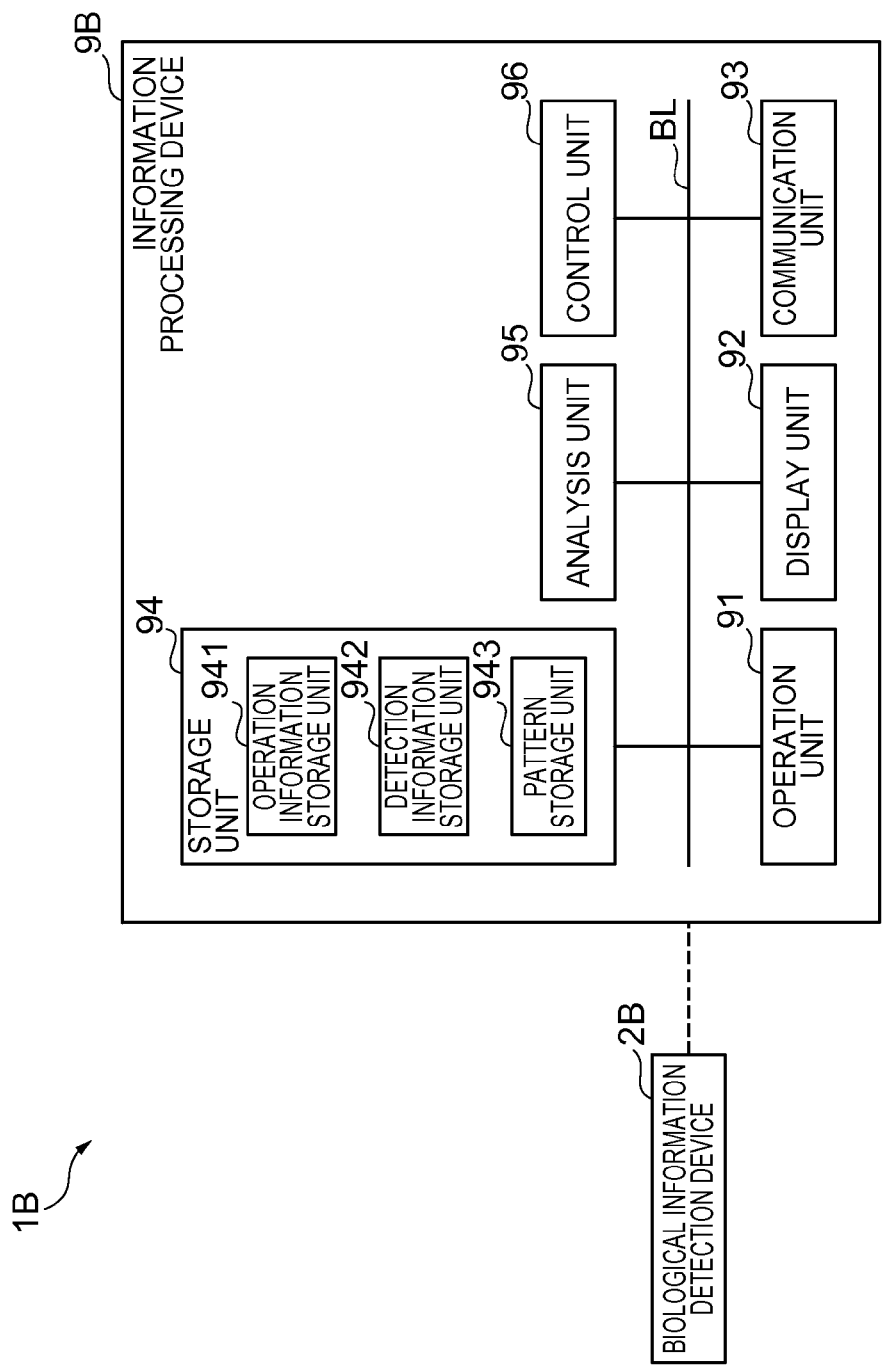
FIG. 7 is a block diagram illustrating a configuration of an information processing device according to the second embodiment.

FIG. 7 is a block diagram illustrating a configuration of the information processing device 9B.

Similarly to the information processing device 9A, the information processing device 9B is constituted by an information processing device such as, for example, a PC (a server is included), a smartphone, and a tablet. The information processing device 9B stores biological information and body motion information which are received from the detection device 2B, and analyzes and stores the pieces of information. In addition, the information processing device 9B performs a process of updating the stored state identification pattern mentioned above and the above-mentioned prediction determination process, and transmits notification information to the detection device 2B when it is determined that a premonitory symptom of seizure has occurred.

The information processing device 9B includes an operation unit 91, a display unit 92, a communication unit 93, a storage unit 94, an analysis unit 95, and a control unit 96.

The operation unit 91 is constituted by a keyboard, a pointing device, a touch panel, or the like, and outputs an operation signal according to a user's input operation to the control unit 96.

The display unit 92 is constituted by various types of displays such as liquid crystal, and displays an operation screen of the information processing device 9B.

The communication unit 93 includes a module capable of communicating with the detection device 2B, and transmits and receives information to and from the detection device 2B under the control of the control unit 27B. For example, the communication unit 93 receives biological information and body motion information from the detection device 2B, stores the biological information and the body motion information in the storage unit 94, and outputs seizure occurrence information to the control unit 96 when receiving the seizure occurrence information from the detection device 2B. Further, the communication unit 93 transmits notification information input from the control unit 96, to the detection device 2B.

Similarly to the storage unit 25A, the storage unit 94 includes an operation information storage unit 941, a detection information storage unit 942, and a pattern storage unit 943.

The operation information storage unit 941 stores operation information such as various types of programs and data which are necessary for the operation of the information processing device 9B. As the operation information, the operation information storage unit 941 stores a control program such as an operating system (OS) that controls the operation of the information processing device 9B, and programs for independently performing an updating process and a prediction determination process of an abnormality prediction process.

The detection information storage unit 942 stores pieces of detection information including the biological information and the body motion information received from the detection device 2B, detection time information indicating a time when the pieces of information are detected, and analysis results of the analysis unit 95 to be described later.

The pattern storage unit 943 is equivalent to a premonitory pattern storage unit and a normal pattern storage unit according to the invention, and stores the above-mentioned state identification patterns. The state identification patterns are frequently updated by the control unit 96 to be described later.

Similarly to the analysis unit 26, the analysis unit 95 analyzes the biological information (pulse wave signal) and the body motion information (acceleration signal) for each predetermined period of time which are acquired from the detection device 2B and calculates the above-mentioned various types of parameters. The analysis unit 95 stores the calculated various types of parameters in the detection information storage unit 942 as analysis results of the analysis unit 95.

Figure 8:
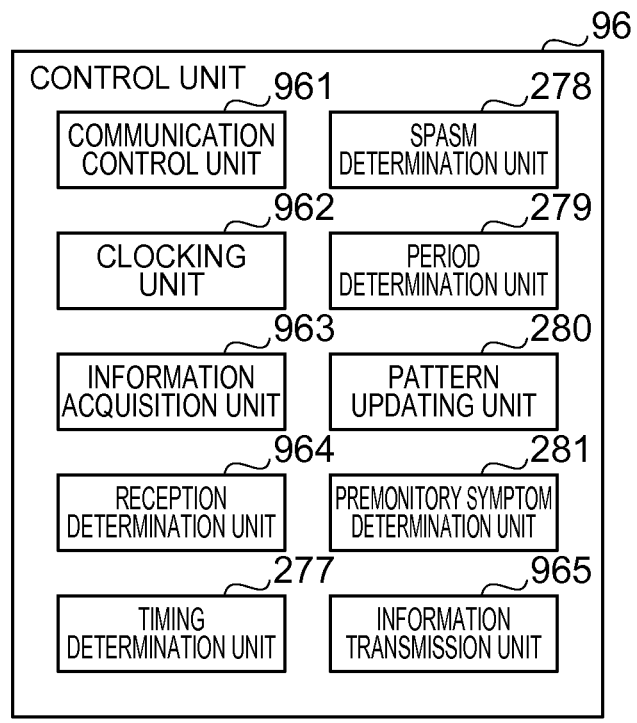
FIG. 8 is a block diagram illustrating a configuration of a control unit of an information processing device according to the second embodiment.

FIG. 8 is a block diagram illustrating a configuration of the control unit 96.

The control unit 96 includes a processing circuit such as a CPU, and controls an operation of the information processing device 9B autonomously or in response to an operation signal which is input from the operation unit 91. For example, the control unit 96 performs an abnormality prediction process to be described later, updates the state identification patterns on the basis of the analysis results of the analysis unit 95, and transmits notification information when it is determined that a premonitory symptom of seizure has occurred and it is determined that seizure has occurred.

The control unit 96 includes a communication control unit 961, a clocking unit 962, an information acquisition unit 963, a reception determination unit 964, a timing determination unit 277, a seizure determination unit 278, a period determination unit 279, a pattern updating unit 280, a premonitory symptom determination unit 281, and an information transmission unit 965, as illustrated in FIG. 8, as functional units which are realized by the processing circuit executing programs stored in the operation information storage unit 941.

The communication control unit 961 controls an operation of the communication unit 93.

The clocking unit 962 clocks the present date and time.

The information acquisition unit 963 functions when the information processing device 9B performs an abnormality prediction process, and acquires detection information stored in the detection information storage unit 942.

The reception determination unit 964 determines whether seizure occurrence information has been received from the detection device 2B.

The timing determination unit 277, the seizure determination unit 278, the period determination unit 279, the pattern updating unit 280, and the premonitory symptom determination unit 281 function as described above.

The information transmission unit 965 is equivalent to a notification information transmission unit according to the invention. When the premonitory symptom determination unit 281 determines that a premonitory symptom has occurred in a user, the information transmission unit 965 transmits notification information, including a message indicating that there is a high possibility of the seizure occurring in the future, to the detection device 2B through the communication unit 93. In addition, when the seizure determination unit 278 determines that seizure has occurred in the user, the information transmission unit 965 transmits notification information, including a message indicating that the seizure has occurred, to the detection device 2B through the communication unit 93.

Abnormality Prediction Process

The information processing device 9B performs an abnormality prediction process according to programs stored in the operation information storage unit 941. The abnormality prediction process includes an updating process and a prediction determination process which are described below.

Updating Process

In an updating process performed by the information processing device 9B according to this embodiment, a seizure pattern, a premonitory pattern, and a normal pattern stored in the pattern storage unit 943 are updated by the same flow as that of the updating process performed by the detection device 2A.

Specifically, in the updating process according to this embodiment, in step SA1 in FIG. 3, the reception determination unit 964 determines whether seizure occurrence information has been received from the detection device 2B.

Here, when the reception determination unit 964 determines that the seizure occurrence information has been received, the pattern updating unit 280 extracts a premonitory pattern and a seizure pattern as described above in step SA7 and step SA8, and the premonitory pattern and the seizure pattern stored in the pattern storage unit 943 are updated on the basis of the premonitory pattern and the seizure pattern.

Thereafter, the process is returned to step SA1.

When it is determined in the determination process of step SA1 that the seizure occurrence information has not been received, in step SA2, the timing determination unit 277 determines whether a determination timing when the occurrence of seizure is determined is set.

When it is determined in the determination process that the determination timing is not set, the process is returned to step SA1 by the control unit 96.

On the other hand, when it is determined that the determination timing is set, the above-mentioned up-to-date detection information is acquired by the information acquisition unit 963 in step SA3.

In step SA4, the seizure determination unit 278 determines whether seizure has occurred in a user.

When it is determined in the determination process of step SA4 that seizure has occurred, the process proceeds to step SA7 and step SA8, and the premonitory pattern and the seizure pattern are updated by the pattern updating unit 280 as described above. In addition, the information transmission unit 965 transmits notification information indicating that seizure has occurred, to the detection device 2B and the like.

Thereafter, the process is returned to step SA1.

When it is determined in the determination process of step SA4 that seizure has not occurred, in step SA5, the period determination unit 279 determines whether a predetermined period of time during which it is determined that seizure has not occurred has elapsed.

When it is determined in the determination process of step SA5 that the predetermined period of time has not elapsed, the process returns to step SA1.

On the other hand, when it is determined in the determination process of step SA5 that the predetermined period of time has elapsed, in step SA6, the pattern updating unit 280 extracts a normal pattern based on detection information which is detected and analyzed during the predetermined period of time, and updates the normal pattern stored in the pattern storage unit 943 on the basis of the normal pattern.

Thereafter, the process returns to step SA1.

Similarly to the updating process described in the first embodiment, such an updating process is repeatedly performed by the control unit 96, and thus updating to state identification patterns based on the detected detection information is performed.

Meanwhile, as described in the first embodiment, the control unit 96 is not limited to a configuration in which the control unit includes both the signal determination unit 276 and the timing and seizure determination units 277 and 278, and may be configured to include either of them.

Prediction Determination Process

A prediction determination process performed by the information processing device 9B according to this embodiment is a process in which it is determined whether a premonitory symptom of seizure has occurred in a user by the same flow as that of the prediction determination process performed by the detection device 2A, and the above-mentioned notification information is transmitted to the detection device 2B when it is determined that the premonitory symptom has occurred.

Specifically, in the prediction determination process according to this embodiment, up-to-date detection information (detection information which is detected and analyzed during the latest predetermined period of time) is acquired by the information acquisition unit 963 in step SB1 of FIG. 4.

Thereafter, in step SB2, the premonitory symptom determination unit 281 determines whether a premonitory symptom of seizure has occurred in a user on the basis of a pattern based on the acquired up-to-date detection information and the premonitory pattern and the normal pattern which are stored in the pattern storage unit 943.

When it is determined in the determination process of step SB2 that a premonitory symptom has not occurred, the control unit 96 terminates the prediction determination process and prepares for the subsequent execution of the prediction determination process.

On the other hand, when it is determined in the determination process of step SB2 that a premonitory symptom has occurred, the information transmission unit 965 transmits the notification information to the detection device 2B in step SB3, and thus the notification unit 23 of the detection device 2B gives notice of the notification information.

In this manner, the prediction determination process is terminated.

Effects of Second Embodiment

According to the biological information measuring system 1B of this embodiment described above, it is possible to exhibit the same effects as those of the biological information measuring system 1A and to exhibit the following effects.

The detection device 2B transmits the biological information and operation information detected to the information processing device 9B, and the information processing device 9B updates the above-mentioned state identification patterns and determines the occurrence of a premonitory symptom. When the detection device 2B receives notification information from the information processing device 9B, the notification unit 23 gives notices of the notification information. Thereby, it is possible to simplify the configuration of the detection device 2B. Therefore, the detection device 2B can be further reduced in size, and thus it is possible to configure the detection device 2B that does not more reliably disturb user's daily action. In addition, since it is possible to save power of the detection device 2B and to operate the detection device 2B for a long period of time using a battery, the convenience of the biological information measuring system 1B can be improved.

Modification of Second Embodiment

The information processing device 9B is configured to include the analysis unit 95 that analyzes the biological information and the body motion information which are included in the detection information received from the detection device 2B. However, similarly to the detection device 2A, the detection device 2B may include the analysis unit 26. In this case, the detection device 2B may transmit the detection information including the analysis results of the analysis unit 26 to the information processing device 9B together with the biological information and the body motion information which are detected by the detection unit 22, and the information processing device 9B may store the received detection information in the detection information storage unit 942.

Third Embodiment

Next, a third embodiment of the invention will be described with reference to the accompanying drawings.

Schematic Configuration of Biological Information Measuring System

Figure 9:
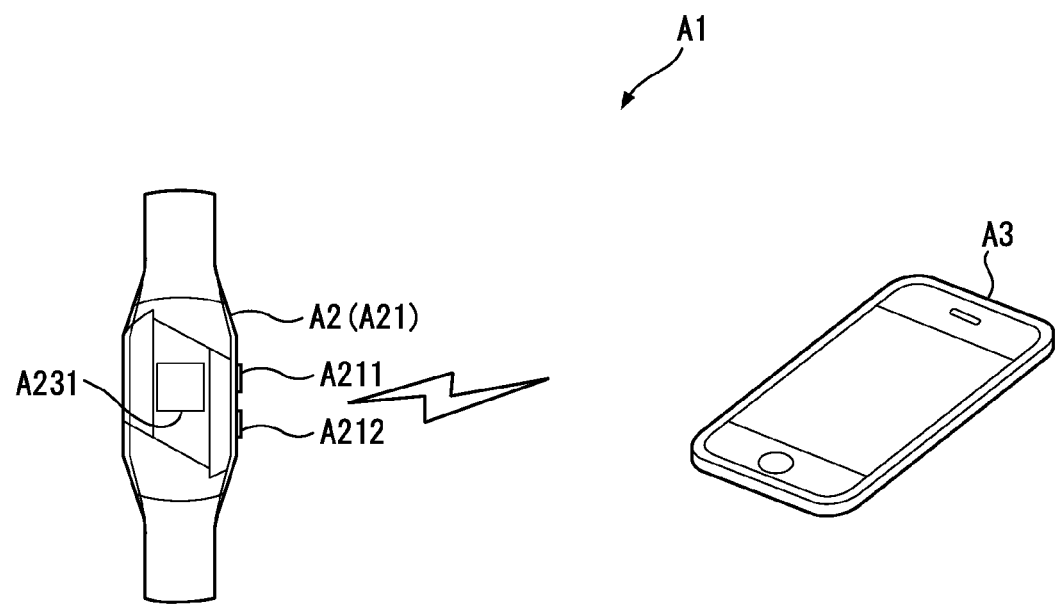
FIG. 9 is a schematic diagram illustrating a configuration of a biological information measuring system according to a third embodiment of the invention.

FIG. 9 is a block diagram illustrating a configuration of a biological information measuring system A1 according to this embodiment.

As illustrated in FIG. 9, the biological information measuring system A1 according to this embodiment includes a biological information measuring device (hereinafter, may be simply referred to as a measurement device) A2 and an information processing device A3 that communicates with the measurement device A2.

For example, the biological information measuring system A1 is used by users required to be watched at all times (specifically, people having a chronic disease (an angina pectoris patient, an arrhythmia patient, and the like) who may cause fainting, tumbling, and a severe symptom, and aged people). The biological information measuring system A1 detects in advance a possibility of abnormality occurring due to deterioration in the pathologic condition when a user is alone or goes out by using the measurement device A2, and notifies the user, a person around the user, and a person monitoring the user of the purport by using the measurement device A2 and the information processing device A3.

Specifically, in the biological information measuring system A1, a motion amount (specifically, an activity amount) in user's daily life is calculated on the basis of biological information and body motion information detected by the measurement device A2, and a warning is given notice of when it is determined that there is a high possibility of abnormality occurring in a user, on the basis of the motion amount.

Meanwhile, the motion amount is a motion amount of action in daily life, and the action is not limited to a motion such as walking, running, and sports and indicates the overall action of moving the body.

Hereinafter, configurations of the measurement device A2 and the information processing device A3 will be described.

Configuration of Biological Information Measuring Device

Figure 10:
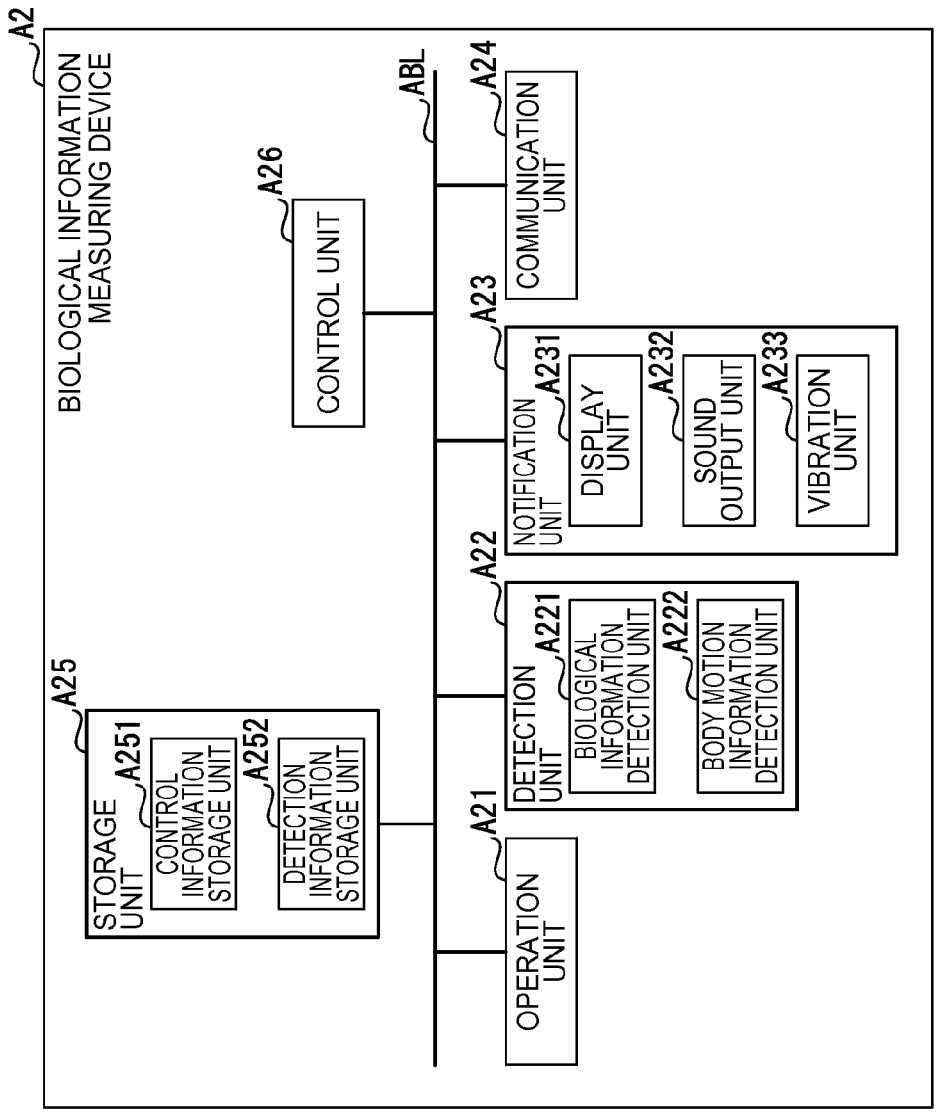
FIG. 10 is a block diagram illustrating a configuration of a biological information measuring device according to the third embodiment.

FIG. 10 is a block diagram illustrating a configuration of the biological information measuring device A2.

The biological information measuring device A2 is a wearable device which is worn on the user and detects and analyzes biological information and body motion information of the user. As illustrated in FIG. 10, the measurement device A2 includes an operation unit A21, a detection unit A22, a notification unit A23, a communication unit A24, a storage unit A25, and a control unit A26, which are connected to each other through a bus line ABL.

Configuration of Operation Unit

The operation unit A21 includes a plurality of buttons A211 and A212 (see FIG. 9) which are disposed at an exterior case of the measurement device A2, and outputs an operation signal according to the button input (pressed) to the control unit A26. Meanwhile, the operation unit A21 is not limited to being configured to include a button, and may be configured to detect a touch panel disposed on a display unit A231 to be described later or a user's tap operation.

Configuration of Detection Unit

The detection unit A22 includes a biological information detection unit A221 and a body motion information detection unit A222.

The biological information detection unit A221 detects biological information of a user under the control of the control unit A26, and outputs the biological information to the control unit A26. The biological information detection unit A221 detects a pulse wave as biological information, but may be configured to further detect blood pressure, a blood sugar level, body temperature, the amount of perspiration, and the like.

The body motion information detection unit A222 detects body motion information indicating the body motion of a user under the control of the control unit A26, and outputs the body motion information to the control unit A26. In this embodiment, the body motion information detection unit A222 detects an acceleration signal varying in association with the body motion of the user, as body motion information. Meanwhile, the body motion information detection unit A222 may detect an angular velocity varying in association with the body motion of the user in addition to acceleration.

Configuration of Notification Unit

The notification unit A23 notifies a user of various types of information under the control of the control unit A26. The notification unit A23 includes a display unit A231, a sound output unit A232, and a vibration unit A233.

The display unit A231 includes a display section such as various types of display panels such as liquid crystal, a plurality of light emitting diodes (LED), or the like, and displays information input from the control unit A26. For example, the display unit A231 displays biological information and body motion information which are detected by the detection unit A22. In addition, the display unit A231 makes the plurality of LEDs function as indicators and turns on and off or lights on and off at least one LED to thereby display a motion intensity calculated on the basis of the biological information and the body motion information. Further, the display unit A231 displays a warning screen based on presentation information generated by the control unit A26, and the like.

The sound output unit A232 is configured to include a sound output section such as a speaker, and outputs a sound according to a sound signal which is input from the control unit A26.

The vibration unit A233 includes a motor of which the operation is controlled by the control unit A26, and notifies a user of, for example, a warning by vibration generated by the driving of the motor.

Configuration of Communication Unit

The communication unit A24 includes a communication module capable of communicating with the information processing device A3. The communication unit A24 regularly transmits the biological information and the body motion information which are detected and acquired to the information processing device A3. Meanwhile, in this embodiment, the communication unit A24 communicates with the information processing device A3 in a wireless manner using a short distance radio communication system, but may communicate with the information processing device A3 through a relay device such as a cradle or may communicate with the information processing device A3 through a cable. Further, the communication unit A24 may communicate with an external device such as the information processing device A3 through a network.

Configuration of Storage Unit

The storage unit A25 is constituted by a storage section including a flash memory or the like, and includes a control information storage unit A251 and a detection information storage unit A252.

The control information storage unit A251 stores control information such as various types of programs and data which are necessary for an operation of the measurement device A2. The control information storage unit A251 stores a control program for controlling the measurement device A2 and notification control programs for performing notification control processes including a second limit value setting process, a warning notification process, and a limit time notification process, as the programs. The notification control processes will be described later.

In addition, the control information storage unit A251 stores connection information necessary for the communication connection with the information processing device A3 and setting information which is input by a user or the like, as the data. The setting information includes a first limit value and a second limit value which are activity limit values.

The first limit value and the second limit value are indexes compared with a total value of activity amounts integrated according to a motion, and are indexes indicating that there is an increasing possibility of abnormality occurring in a user in the case of reaching the total value.

Among these values, the first limit value is a limit value which is set according to the severity of a user's symptom, and is set and stored by the user or a medical worker.

In addition, the second limit value is a limit value in which the total value obtained by performing integration until a predetermined input operation is performed is set and stored, by a user performing the input operation on the operation unit A21. That is, the second limit value is set as a total value of activity amounts integrated between when the user's motion is started and when the occurrence of abnormality or a sign of abnormality is actually felt.

Further, the setting information includes not only the first limit value and the second limit value but also a before-reaching-limit notification time (3 minutes in the initial state), a before-reaching-limit notification proportion (80 percent in the initial state), a limit activity time (60 minutes in the initial state), and a necessary rest time (3 minutes in the initial state) which are set.

Among these pieces of setting information, the first limit value, the before-reaching-limit notification time, the before-reaching-limit notification proportion, the limit activity time, and the necessary rest time are input and set by a user or a medical worker on a setting screen displayed on the display unit A231.

The detection information storage unit A252 stores the biological information and the body motion information which are detected by the detection unit A22 and analysis results (for example, the number of pulses) of the control unit A26 with respect to the biological information and the body motion information. The detection information storage unit A252 is configured to sequentially store these pieces of information and to overwrite information, which is first stored, with information newly acquired when a storage capacity is not sufficient.

Configuration of Control Unit

Figure 11:
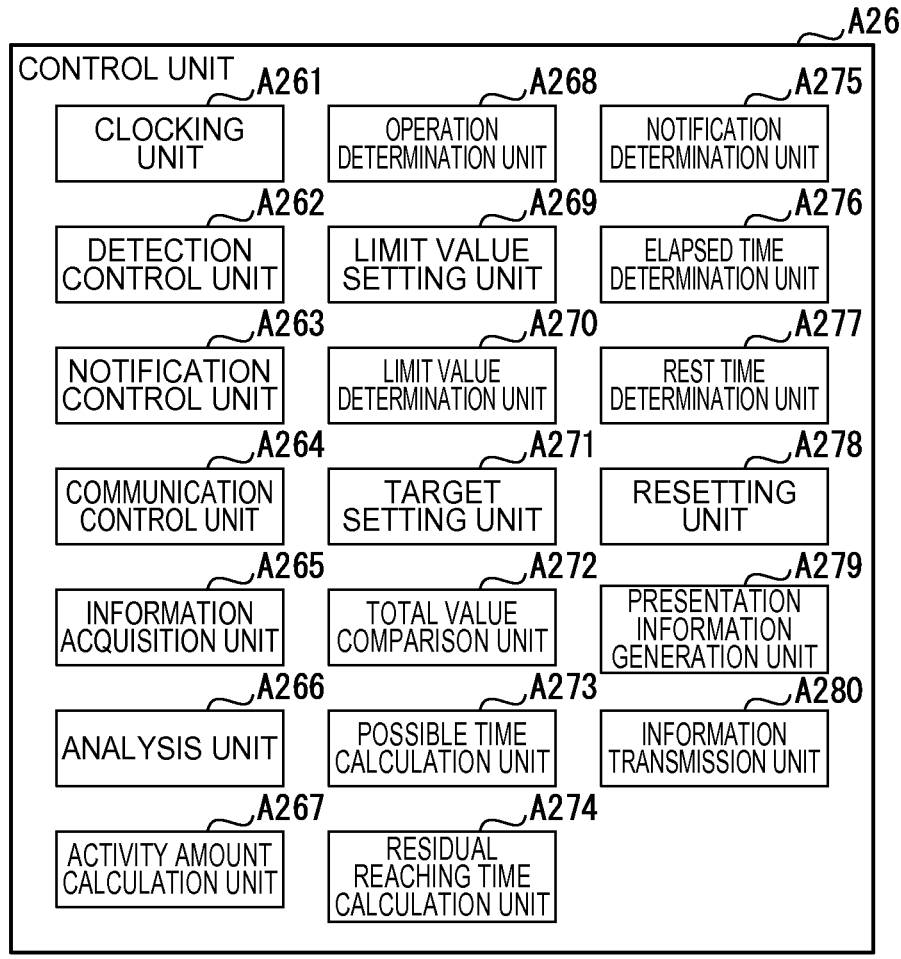
FIG. 11 is a block diagram illustrating a configuration of a control unit according to the third embodiment.

FIG. 11 is a block diagram illustrating a configuration of the control unit A26.

The control unit A26 includes a processing circuit such as a central processing unit (CPU), and controls an operation of the measurement device A2 autonomously or in response to an operation signal which is input from the operation unit A21. The control unit A26 includes a clocking unit A261, a detection control unit A262, a notification control unit A263, a communication control unit A264, an information acquisition unit A265, an analysis unit A266, an activity amount calculation unit A267, an operation determination unit A268, a limit value setting unit A269, a limit value determination unit A270, a target setting unit A271, a total value comparison unit A272, a possible time calculation unit A273, a residual reaching time calculation unit A274, a notification determination unit A275, an elapsed time determination unit A276, a rest time determination unit A277, a resetting unit A278, a presentation information generation unit A279, and an information transmission unit A280, as illustrated in FIG. 11, as functional units realized by the processing circuit executing programs stored in the control information storage unit A251.

The clocking unit A261 clocks the present date and time.

The detection control unit A262 controls an operation of the detection unit 22. For example, when it is determined that the measurement device A2 is not worn on a user, the detection control unit A262 stops the detection of the biological information which is performed by the biological information detection unit A221 to thereby reduce power consumption.

The notification control unit A263 controls an operation of the notification unit A23. For example, the notification control unit A263 outputs an operation state of the measurement device A2 and notification information including a display and a sound which indicate detection results of the detection unit A22 and the like to the notification unit A23 to thereby cause the notification unit A23 notify the notification information. In addition, the notification control unit A263 displays a setting screen for inputting and changing various types of settings of the measurement device A2. Further, the notification control unit A263 drives a motor of the vibration unit A233 as necessary and gives notice of predetermined information by vibration generated by the driving of the motor.

The communication control unit A264 controls an operation of the communication unit A24.

The information acquisition unit A265 acquires various types of signals and pieces of information which are input from the operation unit A21, the detection unit A22, and the communication unit A24. For example, the information acquisition unit A265 acquires contents to be input to the setting screen on the basis of an operation signal according to an input operation with respect to the setting screen. In addition, the information acquisition unit A265 acquires biological information and body motion information which are input from the detection unit A22 to thereby store these pieces of information in the storage unit A25 (detection information storage unit A252).

The analysis unit A266 analyzes biological information and body motion information which are input from the biological information detection unit A221 and the body motion information detection unit A222. Specifically, the analysis unit A266 calculates the number of pulses on the basis of a pulse wave signal which is input from the biological information detection unit A221 and an acceleration signal which is input from the body motion information detection unit A222.

In detail, the analysis unit A266 removes body motion noise components based on the acceleration signal from the pulse wave signal to thereby obtain a pulsation signal. The analysis unit A266 performs frequency analysis such as fast Fourier transform (FFT) on the pulsation signal to extract a frequency based on a pulse from a processing result obtained (power spectrum), and calculates the number of pulses on the basis of the frequency.

The activity amount calculation unit A267 is equivalent to a motion amount calculation unit according to the invention, and calculates an activity amount as a value indicating a user's motion amount. Specifically, the activity amount calculation unit A267 calculates an activity amount (period motion amount) on the basis of biological information and body motion information obtained during one minute as a predetermined period of time. In detail, the activity amount calculation unit A267 calculates an activity amount for the latest one minute as a latest activity amount (latest motion amount) every one minute on the basis of the biological information and the body motion information for the latest one minute.

In addition, the activity amount calculation unit A267 sequentially adds the latest activity amount every one minute to thereby calculate a total value of activity amounts. The total value is reset by the resetting unit A278 to be described later when a user's rest state is continued for a necessary rest time or longer. For this reason, the total value of the activity amounts is set as a total value of activity amounts from when the user's motion is started. Meanwhile, the calculation of an activity amount is disclosed in, for example, JP-A-2003-265441.

The operation determination unit A268 determines a type of input operation performed on the operation unit A21 on the basis of an operation signal which is input from the operation unit A21. For example, the operation determination unit A268 determines whether a setting operation for setting the second limit value has been performed, on the basis of the operation signal.

The limit value setting unit A269 stores the first limit value which is input on the setting screen, in the control information storage unit A251 of the storage unit A25. In addition, when the operation determination unit A268 determines that the setting operation has been performed, the limit value setting unit A269 sets and stores a total value of activity amounts (total value of activity amounts from the start of the user's motion to the present time) which are integrated by the activity amount calculation unit A267, in the control information storage unit A251 as the second limit value. Thereby, when the setting operation is performed even in a case where the second limit value is already set and stored, the stored second limit value is overwritten by the total value. For this reason, a new second limit value may become smaller or larger than the previous second limit value, and may also become larger than the first limit value.

The limit value determination unit A270 compares the first limit value and the second limit value with each other which are stored in the control information storage unit A251, and determines which one of the first limit value and the second limit value is a smaller limit value.

The target setting unit A271 sets a limit value which is compared with the total value calculated by the activity amount calculation unit A267. Specifically, first, the target setting unit A271 firstly sets a limit value, which is determined to be small by the limit value determination unit A270, out of the first limit value and the second limit value, as a comparison object to be compared with the total value. In addition, when the total value comparison unit A272 to be described later determines that the total value exceeds the limit value determined to be small, the target setting unit A271 sets a larger limit value out of the first limit value and the second limit value as a comparison object.

The total value comparison unit A272 compares the comparison object (the first limit value or the second limit value) which is set by the target setting unit A271 with the total value calculated by the activity amount calculation unit A267, and determines which one is larger.

The possible time calculation unit A273 calculates a quotient obtained by dividing the limit value, set as the comparison object by the target setting unit A271, by the latest activity amount calculated by the activity amount calculation unit A267, as a possible time when user's motion can be performed. Here, the latest activity amount is an activity amount for the latest one minute, and thus the possible time is easily obtained by obtaining a quotient by dividing the limit value of the comparison object by the latest activity amount.

The residual reaching time calculation unit A274 calculates a residual reaching time until reaching the limit value set as the comparison object by the target setting unit A271, on the basis of the latest activity amount calculated by the activity amount calculation unit A267 and the total value. For example, the residual reaching time calculation unit A274 calculates a quotient obtained by dividing a value (equivalent to a residual motion amount), which is obtained by subtracting the total value from the limit value, by the latest activity amount as a residual reaching time. That is, the residual reaching time is an estimated value of a residual time until reaching the limit value of the comparison object when the motion having the latest activity amount is continued.

The notification determination unit A275 determines whether there is an increasing possibility of abnormality occurring in a user. Specifically, the notification determination unit A275 determines whether the possibility is increasing by determining whether notification conditions for notifying the user of a warning are satisfied, and determines whether the warning should be given notice of. The notification determination unit A275 functions whenever the latest activity amount is calculated every one minute by the activity amount calculation unit A267. That is, in this embodiment, the notification determination unit A275 performs a determination process every one minute.

Such notification conditions include a condition in which the residual reaching time calculated by the residual reaching time calculation unit A274 reaches the before-reaching-limit notification time stored in the storage unit A25.

In addition, the notification conditions include a condition in which the total value reaches the before-reaching-limit notification proportion of the limit value of the comparison object.

Further, the notification conditions include a condition in which the total value exceeds each of the first limit value and the second limit value.

When at least one of the three notification conditions is satisfied, the notification determination unit A275 determines that a warning should be given notice of due to an increasing possibility of abnormality occurring in a user.

The elapsed time determination unit A276 determines whether an elapsed time since user's motion has been started after the user takes a rest satisfying the necessary rest time reaches the limit activity time.

The rest time determination unit A277 calculates a rest time which is a time when a user is resting on the basis of the detected biological information and body motion information, and determines whether the rest time has reached the necessary rest time. That is, the rest time determination unit A277 determines whether the user has taken a rest for the necessary rest time or longer.

When the rest time determination unit A277 determines that the rest time has reached the necessary rest time, the resetting unit A278 resets the total value of the activity amounts integrated by the activity amount calculation unit A267.

The presentation information generation unit A279 generates presentation information to be presented to a user, and notifies the notification unit A23 of the presentation information by the notification control unit A263.

Specifically, the presentation information generation unit A279 generates presentation information including the possible time calculated by the possible time calculation unit A273.

In addition, when the notification determination unit A275 determines that a warning should be given notice of, the presentation information generation unit A279 generates presentation information to be presented to a user. At this time, the presentation information generation unit A279 generates different presentation information on the basis of whether the comparison object used in the determination process is set to be a smaller limit value or a larger limit value out of the first limit value and the second limit value. For example, presentation information having an implication of attention is indicated in a case of being based on a smaller limit value, and presentation information having an implication of a warning is indicated in a case of being based on a larger limit value. Thereby, a user can ascertain which limit value the presentation information is based on.

In a case where the information transmission unit A280 can communicate with the information processing device A3 through the communication unit A24, the information transmission unit successively transmits pieces of information (detected biological information and body motion information, and analysis results of the analysis unit A266) which are stored in the detection information storage unit A252 to the information processing device A3.

When the notification determination unit A275 determines that a warning should be given notice of, the information transmission unit A280 transmits instruction information for giving notice of predetermined information to the information processing device A3.

Notification Control Process

The control unit A26 described above executes the notification control programs stored in the control information storage unit A251 to thereby independently execute the second limit value setting process, the warning notification process, and the limit time notification process included in the notification control processes. That is, the notification control processes are processes including a warning notification method according to the invention.

Hereinafter, the processes will be described.

Second Limit Value Setting Process

Figure 12:
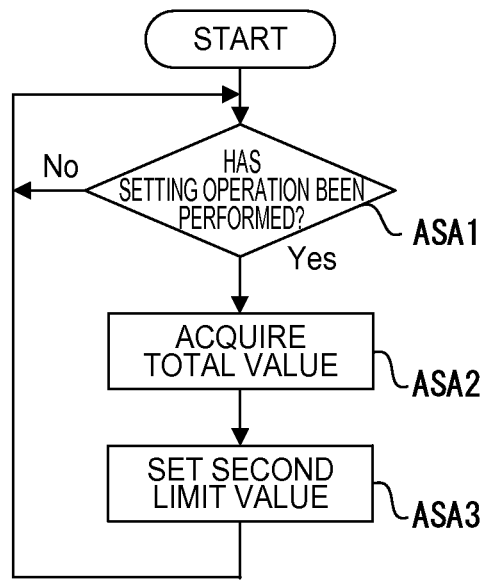
FIG. 12 is a flow chart illustrating a second limit value setting process according to the third embodiment.

FIG. 12 is a flow chart illustrating the second limit value setting process.

The second limit value setting process is a process of setting a total value of activity amounts integrated by the activity amount calculation unit A267 as a second limit value, according to a user's predetermined input operation.

In the second limit value setting process, as illustrated in FIG. 12, first, the operation determination unit A268 determines whether a setting operation for setting the second limit value has been performed, on the basis of an operation signal which is input from the operation unit A21 (step ASA1).

Here, when it is determined that the setting operation has not been performed, the operation determination unit A268 performs the determination process.

On the other hand, when it is determined that the setting operation has been performed, the limit value setting unit A269 acquires the total value (total value of activity amounts integrated since the user's motion has been started) which is obtained by performing integration by the activity amount calculation unit A267 (step ASA2).

The limit value setting unit A269 stores the total value in the control information storage unit A251 as the second limit value to thereby set the second limit value (step ASA3).

After step ASA3 is performed, the process returns to step ASA1.

In this manner, the second limit value setting process is repeatedly performed. When the setting operation is performed, the acquired total value is set as the second limit value.

Warning Notification Process

Figure 13:
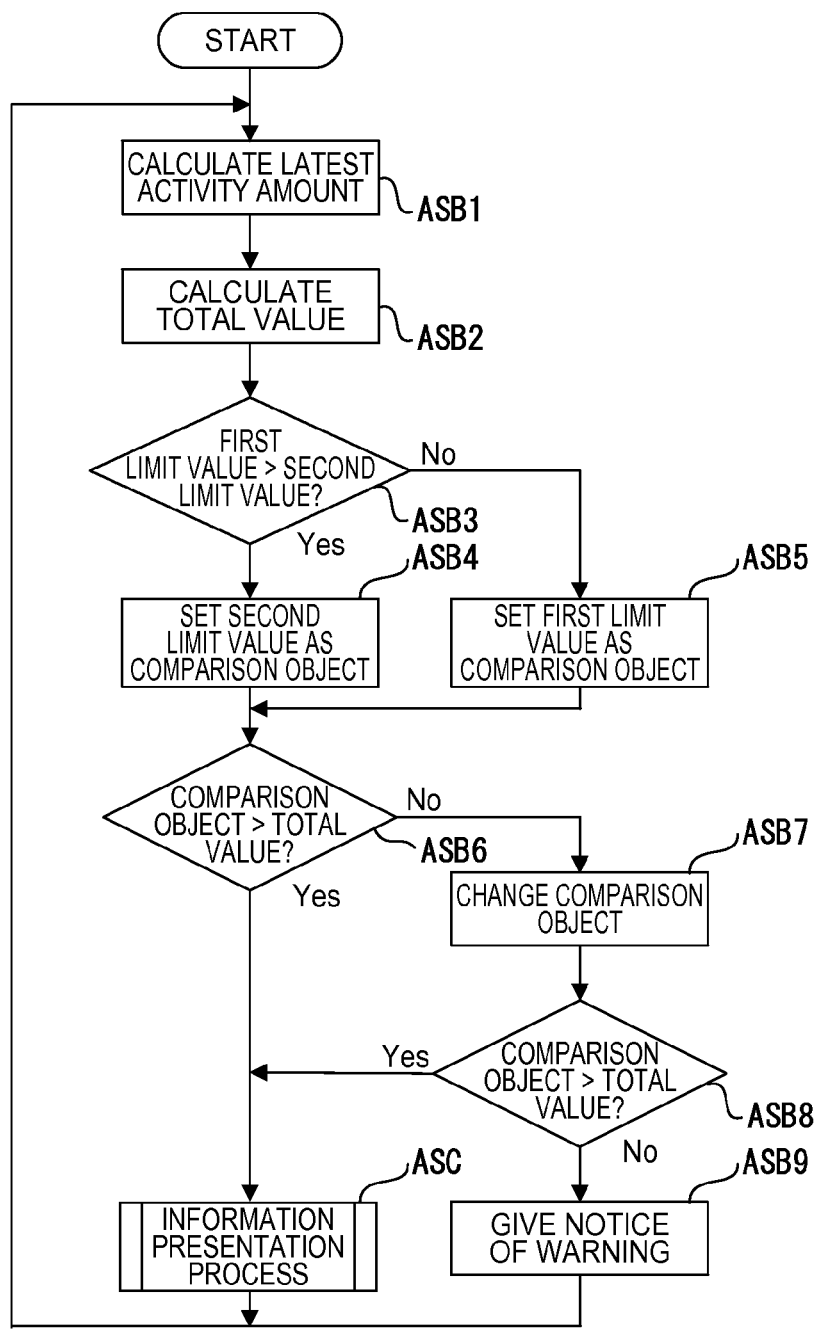
FIG. 13 is a flow chart illustrating a warning notification process according to the third embodiment.

FIG. 13 is a flow chart illustrating the warning notification process.

The warning notification process is a process notifying a user of a warning or a possible time when user's motion can be performed, on the basis of the first limit value and the second limit value mentioned above and a user's present latest activity amount.

In the warning notification process, as illustrated in FIG. 13, first, the activity amount calculation unit A267 calculates the latest activity amount (step ASB1), and integrates the latest activity amount to thereby calculate a total value of activity amounts since the start of the user's motion (step ASB2).

In addition, the limit value determination unit A270 determines whether the first limit value is larger than the second limit value, out of the first limit value and the second limit value stored in the control information storage unit A251 (step ASB3).

In the determination process, when it is determined that the first limit value is larger than the second limit value, the target setting unit A271 sets the second limit value as a comparison object (step ASB4).

On the other hand, in the determination process, when it is determined that the first limit value is not larger than the second limit value, the target setting unit A271 sets the first limit value as a comparison object (step ASB5).

After step ASB4 and step ASB5 are performed, the total value comparison unit A272 compares the limit value of the comparison object with the total value to thereby determine whether the limit value of the comparison object is larger than the total value (step ASB6).

In the determination process, when it is determined that the limit value of the comparison object is larger than the total value, the process proceeds to an information presentation process ASC to be described later.

On the other hand, in the determination process, when it is determined that the limit value of the comparison object is not larger than the total value, the target setting unit A271 changes a larger limit value out of the first limit value and the second limit value to the limit value of the comparison object (step ASB7).

The total value comparison unit A272 determines again whether the limit value of the comparison object is larger than the total value (step ASB8).

Figure 14:
FIG. 14 is a diagram illustrating an example of a warning screen according to the third embodiment.

FIG. 14 is a diagram illustrating an example of a warning screen AWS1.

In the determination process of step ASB8, when it is determined that the limit value of the comparison object is smaller than the total value, that is, when it is determined that the total value has reached a larger limit value out of the first limit value and the second limit value, the presentation information generation unit A279 generates presentation information including a message indicating that the total value exceeds both the first limit value and the second limit value and that it is necessary to take a rest at once, and gives notice of the presentation information (step ASB9). In addition, the information transmission unit A280 transmits the instruction information to the information processing device A3.

By step ASB9, for example, as illustrated in FIG. 14, the warning screen AWS1 including the message is displayed on the display unit A231, the sound output unit A232 gives notice of a warning sound, and the vibration unit A233 generates vibration. Meanwhile, the above-mentioned necessary rest time is set in m of "m minutes" included in the message of the warning screen AWS1.

After step ASB3 is performed, the process returns to step ASB1 to repeatedly perform the warning notification process.

On the other hand, in the determination process of step ASB8, when it is determined that the limit value of the comparison object is larger than the total value, the process proceeds to the information presentation process ASC.

Information Presentation Process

Figure 15:
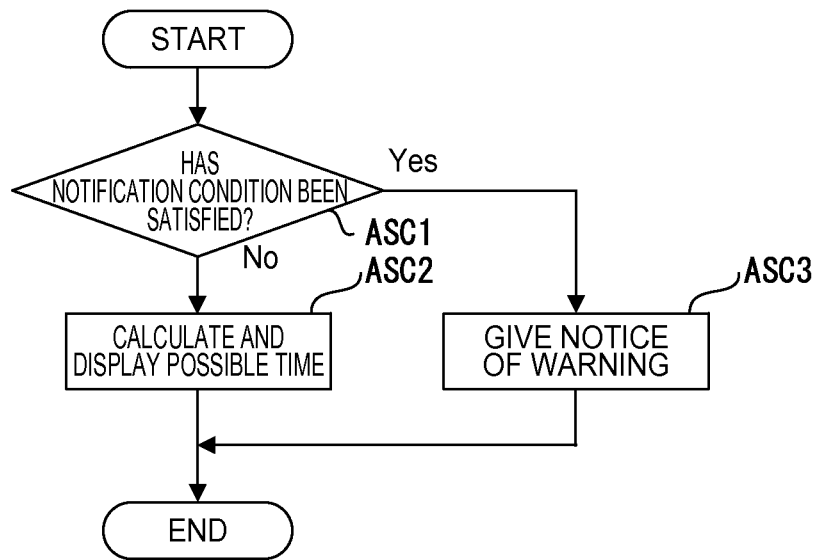
FIG. 15 is a flow chart illustrating an information presentation process according to the third embodiment.

FIG. 15 is a flowchart illustrating the information presentation process ASC.

The information presentation process ASC is a process of changing presentation information to be presented to a user and presenting the information on the basis of whether the notification conditions are satisfied.

In the information presentation process ASC, as illustrated in FIG. 15, the notification determination unit A275 determines whether at least one of a notification condition in which the residual reaching time calculated by the residual reaching time calculation unit A274 reaches the before-reaching-limit notification time stored in the storage unit A25 and a notification condition in which the total value reaches the before-reaching-limit notification proportion of the limit value of the comparison object has been satisfied (step ASC1).

In the determination process of step ASC1, when it is determined that each of the notification conditions is satisfied, the possible time calculation unit A273 calculates a quotient, obtained by dividing the limit value of the comparison object by the latest activity amount, as a possible time as described above, and the presentation information generation unit A279 generates presentation information including the possible time to thereby display the presentation information on the display unit A231 (step ASC2).

Figure 16:
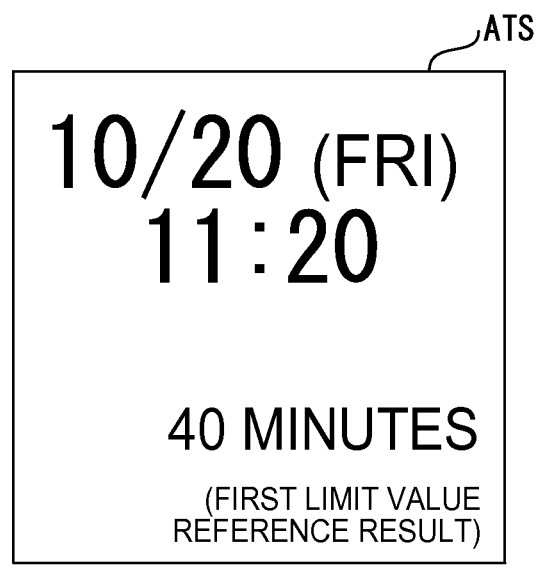
FIG. 16 is a diagram illustrating an example of a time display screen according to the third embodiment.

FIG. 16 is a diagram illustrating an example of a time display screen ATS.

By step ASC2, for example, as illustrated in FIG. 16, the time display screen ATS including a possible time calculated is displayed. The time display screen ATS includes not only the possible time but also the present date and time clocked by the clocking unit A261. In addition, the time display screen ATS includes a display indicating which one between the first limit value and second limit value the limit value of the comparison object is set as.

A user can ascertain a standard indicating to what degree a user can perform motion having the present intensity (activity amount), by the time display screen ATS being displayed. Meanwhile, in step ASC2 of this embodiment, notification using the sound output unit A232 and the vibration unit A233 is not executed so as not to receive any disturbance during motion, but the invention is not limited thereto. For example, whenever the possible time changes, notification using the sound output unit A232 and the vibration unit A233 may be executed.

Meanwhile, the possible time displayed in step ASC2 is set as a quotient obtained by dividing the limit value of the comparison object by the latest activity amount calculated every one minute. However, the invention is not limited thereto.

For example, the activity amount calculation unit A267 may calculate an average value of latest activity amounts since the user's motion has been started, and the possible time calculation unit A273 may calculate a quotient, obtained by dividing the limit value of the comparison object by the average value, as a possible time. Thereby, it is possible to calculate and display the possible time in which the strength and weakness of the motion since the user's motion has been started is taken into consideration.

In addition, the possible time calculation unit A273 may calculate the possible time on the basis of a latest activity amount calculated on the basis of biological information and body motion information acquired for the latest one minute from the present point of time, rather than using a latest activity amount calculated every one minute by the activity amount calculation unit A267. However, even in this case, the total value is updated every one minute.

In addition, the time display screen ATS displayed in step ASC2 may include a residual reaching time calculated by the residual reaching time calculation unit A274 instead of the possible time.

Accordingly, a user can easily ascertain how many minutes motion having the present intensity (activity amount) should be performed in order to reach the limit value.

After step ASC2 is performed, the information presentation process is terminated as illustrated in FIG. 15, and the process returns to step ASB1 as illustrated in FIG. 13 to repeatedly perform the warning notification process.

On the other hand, in the determination process of step ASC1, when it is determined that at least one of the two notification conditions has been satisfied, the presentation information generation unit A279 generates presentation information including a warning message for promoting a rest and displays the presentation information on the display unit A231 (step ASC3).

Figure 17:
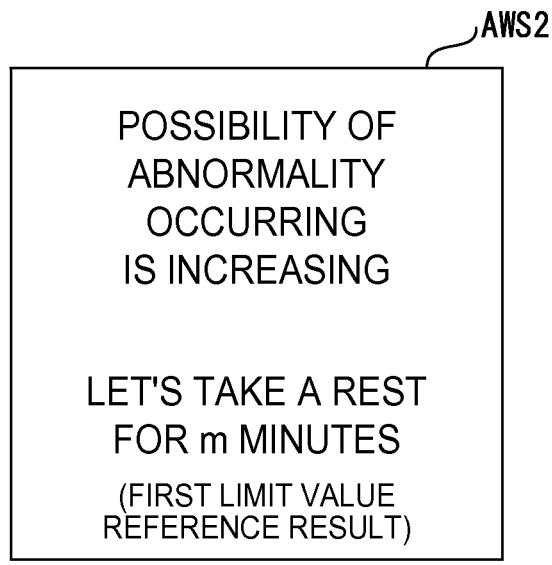
FIG. 17 is a diagram illustrating an example of a warning screen according to the third embodiment.

FIG. 17 is a diagram illustrating an example of a warning screen AWS2.

By step ASC3, for example, as illustrated in FIG. 17, the warning screen AWS2 including the warning message together with the above-mentioned necessary rest time is displayed. The warning screen AWS2 does not include the present date and time in order to allow the warning message to be reliably recognized. On the other hand, the warning screen AWS2 also includes a display indicating which one of the first limit value and the second limit value the limit value of the comparison object is set as.

Meanwhile, as described above, the warning message generated by the presentation information generation unit A279 is different in a case where the comparison object is set as a smaller limit value out of the first limit value and the second limit value and in a case where the comparison object is set as a larger limit value. That is, the warning message is set as contents having an implication of attention when the comparison object is set as a smaller limit value, and is set as contents having an implication of a warning when the comparison object is set as a larger limit value.

It is possible to promote a rest to a user and to suppress the occurrence of abnormality by the warning screen AWS2 being displayed.

In step ASC3 mentioned above, the warning screen AWS2 is displayed, the sound output unit A232 outputs a warning sound, and the vibration unit A233 generates vibration. Further, the information transmission unit A280 transmits the instruction information to the information processing device A3. However, the warning sound output in step ASC3 may have an implication of a warning which is weaker than that of the warning sound output in step ASB9 mentioned above. Similarly, vibration generated in step ASC3 may be vibration (for example, vibration having a low vibration frequency) having an implication of a warning which is weaker than that of the vibration generated in step ASB9 mentioned above.

After step ASC3 is performed, the information presentation process is terminated as illustrated in FIG. 15, and the process returns to step ASB1 as illustrated in FIG. 13 to repeatedly perform the warning notification process.

Limit Time Notification Process

Figure 18:
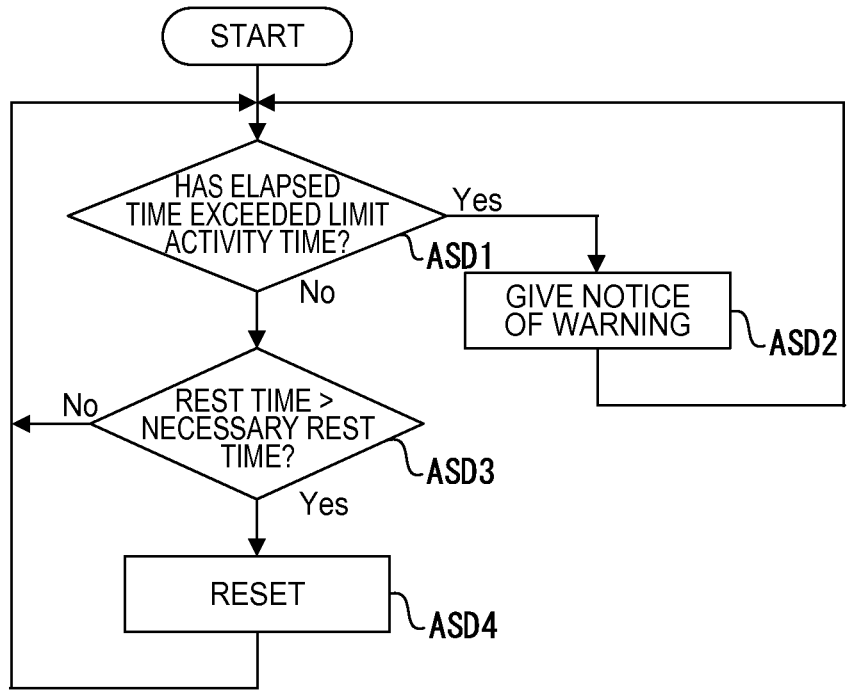
FIG. 18 is a flow chart illustrating a limit time notification process according to the third embodiment.

FIG. 18 is a flow chart illustrating the limit time notification process.

The limit time notification process is a process of giving notice of a warning in a case where an elapsed time since the start of user's motion has reached the limit activity time stored in the control information storage unit A251 and resetting the total value in a case where a time when a user is taking a rest has reached the necessary rest time.

Specifically, in the limit time notification process, as illustrated in FIG. 18, the elapsed time determination unit A276 acquires an elapsed time since the start of user's motion and determines whether the elapsed time has exceeded the limit activity time (step ASD1).

In the determination process, when it is determined that the elapsed time has exceeded the limit activity time, the presentation information generation unit A279 generates the same presentation information as the presentation information included in the warning screen AWS1 to display the same warning screen as the warning screen AWS1 on the display unit A231 (step ASD2). At this time, the information transmission unit A280 transmits the instruction information to the information processing device A3.

After step ASD2 is performed, the process returns to step ASD1.

On the other hand, in the determination process, when it is determined that the elapsed time has not exceeded the limit activity time, the rest time determination unit A277 determines whether a rest time when a user is taking a rest has reached the necessary rest time (step ASD3).

In the determination process, when it is determined that the rest time has not reached the necessary rest time, the process returns to step ASD1.

On the other hand, in the determination process, when it is determined that the rest time has reached the necessary rest time, the resetting unit A278 resets the total value of the activity amounts integrated by the activity amount calculation unit A267 (step ASD4). Thereafter, the process returns to step ASD1.

As described above, since the limit time notification process is repeatedly performed, the total value is continuously reset as long as the user's rest time has reached the necessary rest time, regardless of the calculation and integration of the latest activity amount. In other words, when the user's motion is started from his or her rest state, the resetting of the total value is stopped.

Configuration of Information Processing Device

Referring back to FIG. 9, the information processing device A3 is constituted by a portable terminal device such as a smartphone (multi-functional mobile phone), a tablet, or a PC. When the information processing device receives the above-mentioned instruction information from the measurement device A2, a countermeasure screen to abnormality becoming likely to occur in a user is displayed.

For example, when the information processing device A3 receives the instruction information, the information processing device analyzes the severity of a symptom on the basis of the biological information and the body motion information which are received from the measurement device A2, and displays a countermeasure screen (not shown) which includes a countermeasure method according to the symptom.

Figure 19:
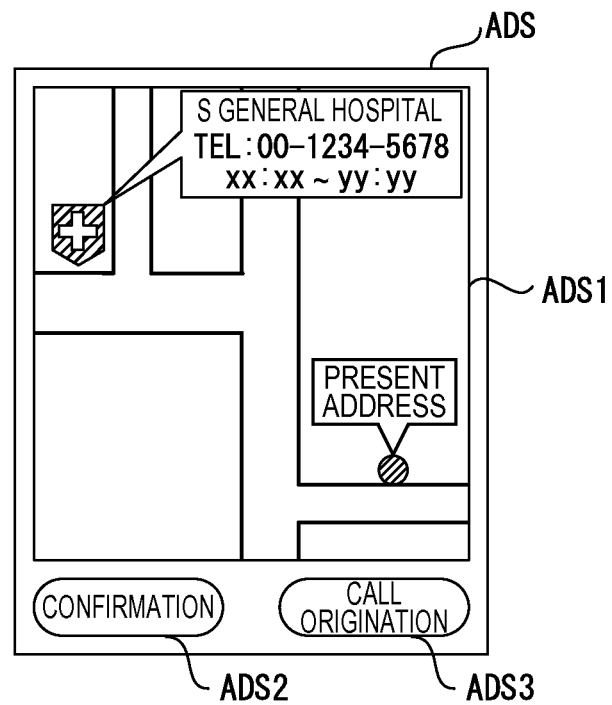
FIG. 19 is a diagram illustrating an example of a countermeasure screen according to the third embodiment.

FIG. 19 is a diagram illustrating an example of a countermeasure screen ADS displayed by the information processing device A3.

In addition, for example, when the information processing device A3 receives the instruction information, the information processing device acquires positional information of the present position (that is, positional information indicating the present position of a user) from a position information satellite or the like. The information processing device A3 searches for a medical institution close to the present position from a server communicable through a network, or the like, on the basis of the positional information. Thereafter, the information processing device A3 displays a countermeasure screen ADS (countermeasure screen ADS illustrated in FIG. 19) in which a mark indicating the location of the medical institution and information such as a contact address of the medical institution are set, on a map ADS1 including the present position.

Further, a confirmation button ADS2 and a call origination button ADS3 are disposed at the countermeasure screen ADS. Among these, when the confirmation button ADS2 is input, the countermeasure screen ADS is closed. On the other hand, when the call origination button ADS3 is input, a call is originated to the contact address of the medical institution displayed.

The countermeasure screen including the countermeasure screen ADS is displayed. Accordingly, even when abnormality occurs in a user, it is possible to carry out a measure for reducing symptoms of abnormality personally or by a surrounding person and to easily make contact with a medical institution.

Meanwhile, in the information processing device A3, information on a medical institution close to a user's present position is searched for and displayed. However, the invention is not limited thereto, and a configuration may be adopted in which a contact address of a medical institution (hospital or emergency center) which is set in advance or a monitoring person is given notice of (displayed). Even in this case, when a call can be originated to the contact address of the medical institution or the monitoring person, it is possible to easily make contact with the medical institution or the monitoring person.

Effects of Third Embodiment

According to the biological information measuring system A1 described above of this embodiment, the following effects are exhibited.

When the notification determination unit A275 determines that there is an increasing possibility of abnormality occurring in a user on the basis of a total value of activity amounts and the first and second limit values, the warning screen AWS2 is displayed on the display unit A231 of the notification unit A23, a warning sound is given notice of by the sound output unit A232, and vibration is generated by the vibration unit A233. Thereby, in a step in which there is an increasing possibility of the abnormality occurring, that is, a step before the abnormality occurs, a warning indicating the purport can be given notice of. Therefore, the user recognizes the warning, and thus it is possible to make it easier to take action for coping with the abnormality. In addition, a monitoring person of a user recognizes the warning, and thus it is possible to give aid to the user.

The notification determination unit A275 determines that there is an increasing possibility of abnormality occurring in a user when the total value of the activity amounts reaches the first limit value or the second limit value a before-reaching-limit notification time before, on the basis of a latest activity amount which is an activity amount for the latest one minute which is a predetermined period of time, and determines that a warning should be given notice of. That is, when motion having the latest activity amount is continued, the notification determination unit A275 determines that there is an increasing possibility of abnormality occurring in a user at a point in time when the total value reaches the first limit value or the second limit value after the elapse of the before-reaching-limit notification time. Thereby, it is possible to notify a user that there is a high possibility of abnormality occurring while securing a postponement time for the user to perform action with respect to abnormality.

The notification determination unit A275 determines that there is an increasing possibility of abnormality occurring when a residual reaching time which is a quotient obtained by dividing a value, obtained by subtracting the total value from the first limit value or the second limit value, by the latest activity amount is set as the before-reaching-limit notification time before (3 minutes before in the initial state). Thereby, it is possible to appropriately calculate a time (residual reaching time) between when motion is started and when a total value of latest activity amounts integrated for every one minute reaches the first limit value or the second limit value. Therefore, it is possible to reliably give notice of the warning the before-reaching-limit notification time before (3 minutes before in the initial state) which is a time when the total value would reach the first limit value or the second limit value. Therefore, it is possible to reliably notify a user that there is a high possibility of abnormality occurring while reliably securing the postponement time.

Since the activity amount calculation unit A267 calculates the activity amounts for the latest one minute as the latest activity amounts, a motion is continued at the present intensity and pace, and thus it is possible to more accurately calculate a time when the total value is expected to reach the limit value. Therefore, it is possible to give notice of the warning at a more appropriate timing.

The notification determination unit A275 determines that there is an increasing possibility of abnormality occurring when the total value has reached a before-reaching-limit notification proportion of the first limit value or the second limit value, and thus the notification unit A23 gives notice of a warning. Thereby, as described above, it is possible to notify a user that there is a high possibility of abnormality occurring while securing a time until the total value reaches the first limit value or the second limit value, that is, a postponement time for a user to perform action with respect to abnormality.

Here, when the postponement time between when the warning is given notice of and when a user performs action (countermeasure action) to abnormality is secured, it is considered that it is not necessary to frequently perform a determination process using the notification determination unit A275 and the notification of the warning using the notification unit A23.

On the other hand, the notification determination unit A275 determines whether the notification conditions have been satisfied every one minute for which the latest activity amount is calculated, and thus it is possible to reduce a processing load of the measurement device A2 and to reduce power consumption.

The determination process of the notification determination unit A275 is performed in two cases of a case where the first limit value is used as a comparison object and a case where the second limit value is used as a comparison object.

Among these, the first limit value is a limit value which is set in advance on the basis of the severity of a user's symptom. For example, the first limit value is a limit value which is set from a medical viewpoint.

On the other hand, the second limit value is a total value of activity amounts integrated between when a user's motion is started and when a predetermined input operation is performed by the user. For example, the second limit value is a total value when the user felt the occurrence of abnormality in the past.

For this reason, the determination process is performed on the basis of each of the first limit value and the second limit value, and the above-mentioned warning is given notice of according to results of the determination process, and thus it is possible to give notice of the warning respectively at the same timing as when the user felt abnormality in the past and a timing when it is determined that there is an increasing possibility of abnormality occurring from a medical viewpoint. Therefore, it is possible to reliably notify that there is an increasing possibility of abnormality occurring in the user.

When it is determined that the above-mentioned notification conditions are not satisfied, that is, there is a low possibility of abnormality occurring in a user, the presentation information generation unit A279 displays the time display screen ATS including a possible time calculated by the possible time calculation unit A273 and a residual reaching time calculated by the residual reaching time calculation unit A274. Thereby, the possible time and the residual reaching time can be used as standard times of a motion permissible to the user until reaching the first limit value or the second limit value. Therefore, the user can easily ascertain a time until a possibility of abnormality occurring is increased.

Here, the activity amount (METs) is set for each type of motion, is a unit indicating the intensity of body activity, and can be calculated on the basis of the body motion information. A motion amount is an exercise value obtained by multiplying the activity amount by a motion time.

Accordingly, the activity amount calculation unit A267 calculates an activity amount as a motion amount of a user, and thus it is possible to more appropriately calculate the motion amount of the user. Therefore, it is possible to reliably give notice of an increase in possibility of abnormality occurring in the user.

When the notification determination unit A275 determines that there is an increasing possibility of the abnormality occurring, the notification unit A23 gives notice of a warning, and the information processing device A3 displays a countermeasure screen including a method of coping with abnormality and a countermeasure screen DS including a contact address of a medical institution close to the present position or a medical institution which is set in advance. Thereby, a user can easily and rapidly make contact with the contact address by the information processing device A3 displaying the countermeasure screens, and it is possible to avoid abnormality from occurring by rapidly performing action shown in the method. Therefore, it is possible to improve the versatility and convenience of the biological information measuring system A1.

Modification of Embodiment

The invention is not limited to the above-described embodiments, and modifications, improvements, and the like in a range capable of accomplishing the object of the invention are included in the invention.

In the first and second embodiments, the biological information measuring systems 1A and 1B are configured to detect seizure including fainting or the like as abnormality occurring in a user and a premonitory symptom of seizure. However, the invention is not limited thereto. That is, the detected abnormality of the user may be another abnormality, and may be, for example, impaired consciousness.

In the first and second embodiments, the detection unit 22 is configured to include the biological information detection unit 221 that detects a pulse wave, a brain wave, electrical activity in the heart, and body temperature of a user as biological information, and the body motion information detection unit 222 that detects acceleration varying in association with the body motion of the user as body motion information. However, the invention is not limited thereto. For example, the detection unit 22 may be configured to include either the biological information detection unit 221 or the body motion information detection unit 222. For example, the detection device may be configured as a body motion information detection device including the body motion information detection unit 222.

In addition, the biological information detection unit 221 may be configured to detect at least one of a pulse wave, a brain wave, electrical activity in the heart, and body temperature without detecting all of them, or may be configured to detect another biological information such as blood pressure instead of or in addition to them. For example, when the detection unit 22 is configured not to include a brain wave sensor that detects a brain wave, the degree of freedom of the positions of the detection devices 2A and 2B worn on a user is increased.

In addition, the detection unit 22 may be configured to further include a positional information detection unit that detects positional information of a user. Such a positional information detection unit corresponds to a satellite positioning system such as a global positioning system (GPS). Examples of the positional information detection unit can include a receiver that acquires positional information on the basis of radio waves received from a satellite and a device that calculates positional information using communication radio waves.

In the first embodiment, the detection device 2A is configured to include the notification unit 23 that gives notice of notification information which is input from the information output unit 282. In the second embodiment, the detection device 2B is configured to include the notification unit 23 that gives notice of notification information which is received from the information processing device 9B. However, the invention is not limited thereto. For example, notification devices connected to the respective detection devices 2A and 2B or a notification device connected to the information processing device 9B may receive and give notice of the notification information, and the information processing devices 9A and 9B may give notice of the notification information.

In addition, the notification unit 23 is not limited to being configured to include all of the display unit 231, the sound output unit 232, and the vibration unit 233, and may be configured to include at least one of them.

In the first and second embodiments, the detection device 2A and the pattern updating unit 280 of the information processing device 9B update each of a seizure pattern, a premonitory pattern, and a normal pattern which are stored in each of the pattern storage units 253 and 943 on the basis of pieces of detection information (biological information, operation information, and the analysis results thereof) which are detected by the detection unit 22 and are stored. However, the invention is not limited thereto. For example, the state identification patterns may not be updated, or at least one of the state identification patterns may be updated.

In the first embodiment, when the signal determination unit 276 determines that the seizure occurrence signal has been input and when the seizure determination unit 278 determines that seizure has occurred in a user, the pattern updating unit 280 updates a premonitory pattern stored in the pattern storage unit 253. In addition, in the second embodiment, when the reception determination unit 964 determines that seizure occurrence information has been received and when the seizure determination unit 278 determines that seizure has occurred in a user, the pattern updating unit 280 updates a premonitory pattern stored in the pattern storage unit 253. However, the invention is not limited thereto. That is, as described above, the premonitory pattern may be updated only in a case where the seizure occurrence signal and the seizure occurrence information are received, or may be updated only in a case where it is determined that seizure has occurred.

In the first and second embodiment, the control units 27A and 96 are notified of the occurrence of seizure according to a user's input operation with respect to the operation unit 21 and are notified of the above-mentioned occurrence time or elapsed time which is input by the user, and the pattern updating unit 280 updates a premonitory pattern on the basis of detection information detected before a starting time of the occurrence time or the elapsed time. However, the invention is not limited thereto. That is, the occurrence time and the elapsed time may not be input.

In the first and second embodiments, when the premonitory symptom determination unit 281 determines that a pattern based on up-to-date detection information is similar to a premonitory pattern between the premonitory pattern and a normal pattern which are stored, the premonitory symptom determination unit determines that a premonitory symptom of seizure has occurred. However, the invention is not limited thereto. That is, when the premonitory symptom determination unit 281 can determine whether a premonitory symptom of seizure has occurred on the basis of at least one of biological information and body motion information of a user detected and the premonitory pattern according to the premonitory symptom, any determination process may be performed. The same is true of the determination of the occurrence of seizure.

In the first and second embodiments, when it is determined that a period during which it is determined that seizure has not occurred has exceeded a predetermined period of time, the pattern updating unit 280 updates a normal pattern stored, on the basis of detection information detected and analyzed during the predetermined period of time. However, the invention is not limited thereto. As described above, the normal pattern may not be updated, and the updating of the normal pattern may be performed using a method different from the above-mentioned method.

In the first and second embodiments, when it is determined that seizure has occurred, the notification unit 23 gives notice of notification information. At this time, the notification information may be given notice of by the notification unit 23, or may be transmitted to an external device connected to a detection device and an information processing device through a network or the like. In this case, it is possible to notify a family or medical worker located at a place away from a user of an occurrence of seizure in the user. In addition, the detection devices 2A and 2B and the information processing devices 9A and 9B may be connected to each other for communication through a network.

In the third embodiment, an activity amount is calculated as a user's motion amount and is used. However, the invention is not limited thereto. That is, an index indicating the intensity of activity may be another index. For example, a value obtained by multiplying a motion intensity by a motion time, which are capable of being calculated on the basis of the biological information and the body motion information may be used as a motion amount.

In addition, when an activity amount can be calculated using the body motion information even when the activity amount is used as a motion amount, biological information may not be detected.

In the third embodiment, an activity amount for one minute is calculated as a period motion amount. However, the invention is not limited thereto. That is, a period during which an activity amount is calculated is not limited to one minute. For example, the period may be a period such as 2 minutes which exceeds one minute, or may be a period such as 30 seconds which is less than one minute. Consequently, the determination process of the notification determination unit A275 may not also be performed every one minute, and may be performed according to a time when the activity amount calculation unit A267 calculates a latest activity amount.

In the third embodiment, the before-reaching-limit notification time is set to be 3 minutes, and the before-reaching-limit notification proportion is set to be 80 percent. However, the invention is not limited thereto, and the time and proportion can be appropriately modified.

In the third embodiment, a first limit value which is set according to the severity of a user's symptom and a second limit value in which the above-mentioned total value when a user felt the occurrence of abnormality in the past is set are set, and the determination process of the notification determination unit A275 is performed using the first limit value and the second limit value. However, the invention is not limited thereto. For example, only one of the first limit value and the second limit value may be set.

In addition, when the second limit value is set to be necessarily smaller than the first limit value, a comparison object may be set as the second limit value without performing step ASB3 to step ASB5 described above.

In the third embodiment, the information processing device A3 capable of communicating with the measurement device A2 displays the countermeasure screen ADS including a method of coping with abnormality and a contact address. However, the invention is not limited thereto. That is, the information processing device A3 may not be provided, and contents of the countermeasure screen displayed by the information processing device A3 may be appropriately modified.

In the third embodiment, when a time when a user is resting reaches a necessary rest time which is set in advance, a total value of activity amounts is reset. However, the invention is not limited thereto. For example, when the state of a user is set to be a rest state, the total value may be decremented according to an elapsed time since the rest state has been set. In addition, a configuration in which the necessary rest time fluctuates depending on the total value and body condition may be adopted.

What is claimed is:

1. An abnormality prediction device comprising:
a detection unit that detects detection information including at least one of biological information of a user and body motion information regarding a body motion of the user;
a premonitory symptom determination unit that determines whether a premonitory symptom has occurred in the user on the basis of the detection information detected by the detection unit and a premonitory pattern which is a pattern of the detection information according to the premonitory symptom of abnormality occurring in the user;
an information output unit that, when the premonitory symptom determination unit determines that the premonitory symptom has occurred, outputs notification information indicating that occurrence of abnormality in the user is predicted;
a premonitory pattern storage unit that stores the premonitory pattern;
a premonitory pattern updating unit that updates the premonitory pattern stored in the premonitory pattern storage unit, on the basis of the detection information detected prior to an occurrence timing of the abnormality when the abnormality has occurred in the user; and
an abnormality determination unit that determines whether abnormality has occurred in the user,
wherein when the abnormality determination unit determines that abnormality has occurred, the premonitory pattern updating unit updates the premonitory pattern.

2. The abnormality prediction device according to claim 1, further comprising a notification unit that notifies the user of the notification information which is input from the information output unit.

3. The abnormality prediction device according to claim 1, further comprising an operation unit that receives an input operation from the user,
wherein when an operation signal indicating that the abnormality has occurred is input from the operation unit, the premonitory pattern updating unit updates the premonitory pattern.

4. The abnormality prediction device according to claim 3,
wherein the operation unit is configured to be able to input either an elapsed time since the abnormality has occurred in the user or an occurrence time of the abnormality, and
wherein the premonitory pattern updating unit updates the premonitory pattern on the basis of the detection information detected before either a starting time of the elapsed time or the occurrence time which is input by the operation unit.

5. The abnormality prediction device according to claim 1,
wherein the premonitory symptom determination unit determines that the premonitory symptom has occurred in the user when a pattern based on the detection information detected by the detection unit in a state where the abnormality has not occurred in the user is similar to the premonitory pattern rather than a normal pattern which is a pattern of the detection information according to a state where the premonitory symptom and the abnormality have not occurred in the user, and determines that the premonitory symptom has not occurred in the user when the pattern is similar to the normal pattern.

6. The abnormality prediction device according to claim 5, further comprising:
a normal pattern storage unit that stores the normal pattern;
an abnormality determination unit that determines whether the abnormality has occurred in the user;
a period determination unit that determines whether a predetermined period of time during which the abnormality determination unit determines that abnormality has not occurred in the user has elapsed; and
a normal pattern updating unit that, when the period determination unit determines that the predetermined period of time has elapsed, updates the normal pattern on the basis of the detection information detected by the detection unit during the predetermined period of time.

7. The abnormality prediction device according to claim 1, wherein when it is determined that the abnormality has occurred in the user, the information output unit outputs information indicating that the abnormality has occurred.

8. The abnormality prediction device according to claim 1,
wherein the detection unit includes at least one of a biological information detection unit that detects a pulse wave of the user as the biological information, and a body motion information detection unit that detects acceleration varying in association with the body motion of the user, as the body motion information.

9. An abnormality prediction system comprising:
a detection device that detects detection information regarding a user; and
an information processing device that processes detection information detected by the detection device,
wherein the detection device includes
a detection unit that detects detection information including at least one of biological information of the user and body motion information regarding a body motion of the user,
a detection information transmission unit that transmits the detection information to the information processing device, and
a notification unit that notifies the user of information received from the information processing device, and
wherein the information processing device includes
a premonitory symptom determination unit that determines whether a premonitory symptom has occurred in the user, on the basis of the detection information received from the detection device and a premonitory pattern which is a pattern of the detection information according to the premonitory symptom of abnormality occurring in the user,
a notification information transmission unit that, when the premonitory symptom determination unit determines that the premonitory symptom has occurred, transmits notification information indicating that occurrence of abnormality in the user is predicted to the detection device,
a premonitory pattern storage unit that stores the premonitory pattern,
a premonitory pattern updating unit that updates the premonitory pattern stored in the premonitory pattern storage unit, on the basis of the detection information detected prior to an occurrence timing of the abnormality when the abnormality has occurred in the user, and
an abnormality determination unit that determines whether abnormality has occurred in the user,
wherein when the abnormality determination unit determines that abnormality has occurred, the premonitory pattern updating unit updates the premonitory pattern.

10. An abnormality prediction method performed using a detection device that detects a state of a user, the method comprising:
detecting detection information including at least one of biological information of a user and body motion information regarding a body motion of the user;
determining whether a premonitory symptom has occurred in the user, on the basis of the detected detection information and a premonitory pattern which is a pattern of the detection information according to the premonitory symptom of abnormality occurring in the user;
outputting, when it is determined that the premonitory symptom has occurred, notification information indicating that occurrence of abnormality in the user is predicted,
storing the premonitory pattern in a premonitory pattern storage unit,
updating the premonitory pattern stored in the premonitory pattern storage unit, on the basis of the detection information detected prior to an occurrence timing of the abnormality when the abnormality has occurred in the user, and
determining whether abnormality has occurred in the user and when it is determined that abnormality has occurred, updating the premonitory pattern stored in the premonitory pattern storage unit.

11. A biological information measuring device comprising:
a biological information detection unit that detects biological information of a user;
a body motion information detection unit that detects body motion information of the user;
a motion amount calculation unit that calculates a motion amount of the user on the basis of the biological information and the body motion information;
a limit value setting unit that sets a limit value of the motion amount according to the user;
a notification determination unit that determines a possibility of abnormality occurring in the user, on the basis of the calculated motion amount and the set limit value;
a notification unit that gives notice of a warning when the notification determination unit determines that there is an increasing possibility of the abnormality occurring,
wherein the motion amount calculation unit calculates a total value of motion amounts since the user's motion has been started and a period motion amount which is a motion amount during a predetermined period of time since the user's motion has been started, and
wherein the notification determination unit determines that there is an increasing possibility of the abnormality occurring, on the basis of the period motion amount, at a predetermined time before the total value reaches the limit value.

12. The biological information measuring device according to claim 11, wherein when a quotient obtained by dividing a residual motion amount, obtained by subtracting the total value from the limit value, by the period motion amount is set to be the predetermined time or less, the notification determination unit determines that there is an increasing possibility of the abnormality occurring.

13. The biological information measuring device according to claim 11, wherein the period motion amount is a motion amount during a latest predetermined period of time.

14. The biological information measuring device according to claim 11,
wherein when the total value has reached a predetermined proportion of the limit value, the notification determination unit determines that there is an increasing possibility of the abnormality occurring.

15. The biological information measuring device according to claim 11, wherein the notification determination unit functions at predetermined time intervals.

16. The biological information measuring device according to claim 11,
wherein the limit value includes a first limit value that is set in advance on the basis of severity of the user's disease, and a second limit value in which motion amounts integrated between when the user's motion is started and when a predetermined input operation is performed are set, and wherein the notification determination unit determines a possibility of the abnormality occurring, on the basis of the calculated motion amount and at least one of the first limit value and the second limit value which are set.

17. The biological information measuring device according to claim 11, wherein the motion amount calculation unit calculates a latest motion amount which is a motion amount during the latest predetermined period of time since the user's motion has been started, and wherein the notification unit gives notice of a time based on a quotient, obtained by dividing the limit value by the latest motion amount, as a time when a motion is able to be performed.

18. The biological information measuring device according to claim 11, wherein the motion amount is an activity amount.

19. A biological information measuring system comprising:

the biological information measuring device according to claim 11; and an information processing device that communicates with the biological information measuring device, wherein when the notification determination unit determines that there is an increasing possibility of the abnormality occurring, the information processing device gives notice of predetermined information.

20. A biological information measuring device comprising:

a biological information detection unit that detects biological information of a user;

a body motion information detection unit that detects body motion information of the user;

a motion amount calculation unit that calculates a motion amount of the user on the basis of the biological information and the body motion information;

a limit value setting unit that sets a limit value of the motion amount according to the user;

a notification determination unit that determines a possibility of abnormality occurring in the user, on the basis of the calculated motion amount and the set limit value; and a notification unit that gives notice of a warning when the notification determination unit determines that there is an increasing possibility of the abnormality occurring, wherein the notification determination unit functions at predetermined time intervals.

* * * * *